(12) United States Patent
Falotico et al.

(10) Patent No.: US 7,300,662 B2
(45) Date of Patent: *Nov. 27, 2007

(54) DRUG/DRUG DELIVERY SYSTEMS FOR THE PREVENTION AND TREATMENT OF VASCULAR DISEASE

(75) Inventors: Robert Falotico, Belle Mead, NJ (US); Gregory A. Kopia, Hillsborough, NJ (US); Gerard H. Llanos, Stewartsville, NJ (US)

(73) Assignee: Cordis Corporation, Miami Lakes, FL (US)

( * ) Notice: Subject to any disclaimer, the term of this patent is extended or adjusted under 35 U.S.C. 154(b) by 503 days.

This patent is subject to a terminal disclaimer.

(21) Appl. No.: 10/829,074

(22) Filed: Apr. 21, 2004

(65) Prior Publication Data

US 2004/0260268 A1    Dec. 23, 2004

Related U.S. Application Data

(63) Continuation-in-part of application No. 09/850,293, filed on May 7, 2001, now abandoned, which is a continuation-in-part of application No. 09/575,480, filed on May 19, 2000.

(60) Provisional application No. 60/263,979, filed on Jan. 25, 2001, provisional application No. 60/263,806, filed on Jan. 24, 2001, provisional application No. 60/262,614, filed on Jan. 18, 2001, provisional application No. 60/262,461, filed on Jan. 18, 2001, provisional application No. 60/204,417, filed on May 12, 2000.

(51) Int. Cl.
*A61F 2/00* (2006.01)
*A61F 2/06* (2006.01)

(52) U.S. Cl. .................... 424/424; 623/1.42; 623/1.45

(58) Field of Classification Search ........ 424/422–426; 623/1.42–1.48
See application file for complete search history.

(56) References Cited

U.S. PATENT DOCUMENTS

| | | | |
|---|---|---|---|
| 861,659 A | 7/1907 | Johnston | 464/147 |
| 3,051,677 A | 8/1962 | Rexford | 522/156 |
| 3,279,996 A | 10/1966 | Long et al. | 424/424 |
| 3,526,005 A | 9/1970 | Bokros | 623/11.11 |
| 3,599,641 A | 8/1971 | Sheridan | 604/256 |

(Continued)

FOREIGN PATENT DOCUMENTS

DE    3205942 A1    9/1983

(Continued)

OTHER PUBLICATIONS

Boston Scientific, "Measuring DES Efficacy," www.taxus-stent.com/usa/efficacy.html, pp. 1-3, copyright 2006.*

(Continued)

*Primary Examiner*—Sharon E. Kennedy
(74) *Attorney, Agent, or Firm*—Woodcock Washburn LLP

(57) ABSTRACT

A drug and drug delivery system may be utilized in the treatment of vascular disease. A local delivery system is coated with rapamycin or other suitable drug, agent or compound and delivered intraluminally for the treatment and prevention of neointimal hyperplasia following percutaneous transluminal coronary angiography. The local delivery of the drugs or agents provides for increased effectiveness and lower systemic toxicity.

25 Claims, 2 Drawing Sheets

U.S. PATENT DOCUMENTS

| | | | |
|---|---|---|---|
| 3,657,744 A | 4/1972 | Ersek | |
| 3,744,596 A | 7/1973 | Sander | 188/203 |
| 3,779,805 A | 12/1973 | Alsberg | 427/105 |
| 3,929,992 A | 12/1975 | Sehgal et al. | 424/122 |
| 3,932,627 A | 1/1976 | Margraf | |
| 3,948,254 A | 4/1976 | Zaffaroni | 128/833 |
| 3,952,334 A | 4/1976 | Bokros et al. | 623/11.11 |
| 3,968,800 A | 7/1976 | Vilasi | 606/198 |
| 4,069,307 A | 1/1978 | Higuchi et al. | 424/432 |
| 4,076,285 A | 2/1978 | Martinez | 285/332 |
| 4,292,965 A | 10/1981 | Nash et al. | |
| 4,299,226 A | 11/1981 | Banka | 604/509 |
| 4,300,244 A | 11/1981 | Bokros | 623/1.13 |
| 4,312,920 A | 1/1982 | Pierce et al. | 428/425.5 |
| 4,321,711 A | 3/1982 | Mano | 623/1.43 |
| 4,323,071 A | 4/1982 | Simpson et al. | 606/194 |
| 4,390,599 A | 6/1983 | Broyles | 428/597 |
| 4,413,359 A | 11/1983 | Akiyama et al. | 623/23.72 |
| 4,423,183 A | 12/1983 | Close | 524/546 |
| 4,441,216 A | 4/1984 | Ionescu et al. | |
| 4,503,569 A | 3/1985 | Dotter | |
| 4,512,338 A | 4/1985 | Balko et al. | 606/108 |
| 4,550,447 A | 11/1985 | Seiler, Jr. et al. | 623/1.32 |
| 4,553,545 A | 11/1985 | Maass et al. | |
| 4,560,374 A | 12/1985 | Hammerslag | 604/509 |
| 4,562,596 A | 1/1986 | Kronberg | 623/1.32 |
| 4,565,740 A | 1/1986 | Golander et al. | 428/409 |
| 4,580,568 A | 4/1986 | Gianturco | |
| 4,613,665 A | 9/1986 | Larm | |
| 4,642,111 A | 2/1987 | Sakamoto et al. | 424/492 |
| 4,655,771 A | 4/1987 | Wallsten | |
| 4,656,083 A | 4/1987 | Hoffman et al. | 442/123 |
| 4,676,241 A | 6/1987 | Webb et al. | 128/207.14 |
| 4,678,466 A | 7/1987 | Rosenwald | 424/427 |
| 4,687,482 A | 8/1987 | Hanson | 623/1.49 |
| 4,689,046 A | 8/1987 | Bokros | 623/2.31 |
| 4,731,054 A | 3/1988 | Billeter et al. | 604/93.01 |
| 4,733,665 A | 3/1988 | Palmaz | |
| 4,739,762 A | 4/1988 | Palmaz | |
| 4,740,207 A | 4/1988 | Kreamer | 623/1.15 |
| 4,749,585 A | 6/1988 | Greco et al. | 428/422 |
| 4,753,652 A | 6/1988 | Langer et al. | 623/1.42 |
| 4,760,849 A | 8/1988 | Kropf | 606/191 |
| 4,768,507 A | 9/1988 | Fischell et al. | 623/1.11 |
| 4,776,337 A | 10/1988 | Palmaz | |
| 4,786,500 A | 11/1988 | Wong | 424/422 |
| 4,787,899 A | 11/1988 | Lazarus | 623/1.11 |
| 4,800,882 A | 1/1989 | Gianturco | |
| 4,810,784 A | 3/1989 | Larm | 536/20 |
| 4,856,516 A | 8/1989 | Hillstead | |
| 4,871,357 A | 10/1989 | Hsu et al. | 604/266 |
| 4,872,867 A | 10/1989 | Joh | |
| 4,876,109 A | 10/1989 | Mayer et al. | 604/269 |
| 4,886,062 A | 12/1989 | Wiktor | |
| 4,907,336 A | 3/1990 | Gianturco | |
| 4,916,193 A | 4/1990 | Tang et al. | |
| 4,954,126 A | 9/1990 | Wallsten | |
| 4,969,458 A | 11/1990 | Wiktor | |
| 4,990,131 A | 2/1991 | Dardik | |
| 4,990,155 A | 2/1991 | Wilkoff | |
| 4,994,071 A | 2/1991 | MacGregor | |
| 4,994,298 A | 2/1991 | Yasuda | 427/490 |
| 4,998,923 A | 3/1991 | Samson et al. | 606/194 |
| 5,015,253 A | 5/1991 | MacGregor | |
| 5,019,090 A | 5/1991 | Pinchuk | 623/1.15 |
| 5,019,096 A | 5/1991 | Fox, Jr. et al. | 600/36 |
| 5,029,877 A | 7/1991 | Fedeli et al. | 277/354 |
| 5,034,265 A | 7/1991 | Hoffman et al. | 442/126 |
| 5,035,706 A | 7/1991 | Gianturco | |
| 5,041,100 A | 8/1991 | Rowland et al. | |
| 5,041,126 A | 8/1991 | Gianturco | |
| 5,047,020 A | 9/1991 | Hsu | 604/266 |
| 5,049,132 A | 9/1991 | Shaffer et al. | |
| 5,049,403 A | 9/1991 | Larm et al. | 427/2.1 |
| 5,053,048 A | 10/1991 | Pinchuk | |
| 5,059,166 A | 10/1991 | Fischell et al. | 600/3 |
| 5,061,275 A | 10/1991 | Wallsten et al. | |
| 5,061,750 A | 10/1991 | Feijen et al. | |
| 5,064,435 A | 11/1991 | Porter | |
| 5,092,877 A | 3/1992 | Pinchuk | |
| 5,102,417 A | 4/1992 | Palmaz | |
| 5,104,404 A | 4/1992 | Wolff | |
| 5,116,365 A | 5/1992 | Hillstead | |
| 5,122,154 A | 6/1992 | Rhodes | |
| 5,131,908 A | 7/1992 | Dardik et al. | |
| 5,133,732 A | 7/1992 | Wiktor | |
| 5,134,192 A | 7/1992 | Feijen et al. | |
| 5,135,536 A | 8/1992 | Hillstead | |
| 5,163,952 A | 11/1992 | Froix | |
| 5,163,958 A | 11/1992 | Pinchuk | |
| 5,171,217 A | 12/1992 | March et al. | 604/507 |
| 5,171,262 A | 12/1992 | MacGregor | |
| 5,176,660 A | 1/1993 | Truckai | |
| 5,176,972 A | 1/1993 | Bloom et al. | 430/14 |
| 5,178,618 A | 1/1993 | Kandarpa | |
| 5,180,366 A | 1/1993 | Woods | |
| 5,182,317 A | 1/1993 | Winters et al. | |
| 5,185,408 A | 2/1993 | Tang et al. | |
| 5,192,307 A | 3/1993 | Wall | |
| 5,195,984 A | 3/1993 | Schalz | |
| 5,202,332 A | 4/1993 | Hughes et al. | 514/291 |
| 5,213,576 A | 5/1993 | Abiuso et al. | |
| 5,213,898 A | 5/1993 | Larm et al. | 428/422 |
| 5,217,483 A | 6/1993 | Tower | |
| 5,222,971 A | 6/1993 | Willard et al. | |
| 5,226,913 A | 7/1993 | Pinchuk | |
| 5,234,456 A | 8/1993 | Silvestrini | |
| 5,246,445 A | 9/1993 | Yachia et al. | |
| 5,258,020 A | 11/1993 | Froix | |
| 5,258,021 A | 11/1993 | Duran | |
| 5,262,451 A | 11/1993 | Winters et al. | |
| 5,266,073 A | 11/1993 | Wall | |
| 5,272,012 A | 12/1993 | Opolski | 428/423.1 |
| 4,733,665 A | 1/1994 | Palmaz | 606/108 |
| 5,275,622 A | 1/1994 | Lazarus et al. | |
| 5,282,823 A | 2/1994 | Schwartz et al. | |
| 5,282,824 A | 2/1994 | Gianturco | |
| 5,283,257 A | 2/1994 | Gregory et al. | |
| 5,288,711 A | 2/1994 | Mitchell et al. | |
| 5,290,305 A | 3/1994 | Inoue | |
| 5,292,331 A | 3/1994 | Boneau | |
| 5,292,802 A | 3/1994 | Rhee et al. | |
| 5,304,121 A | 4/1994 | Sahatjian | |
| 5,304,200 A | 4/1994 | Spaulding | |
| 5,306,250 A | 4/1994 | March et al. | |
| 5,308,862 A | 5/1994 | Ohlstein | |
| 5,308,889 A | 5/1994 | Rhee et al. | |
| 5,314,444 A | 5/1994 | Gianturco | |
| 5,314,472 A | 5/1994 | Fontaine | |
| 5,328,471 A | 7/1994 | Slepian | |
| 5,334,301 A | 8/1994 | Heinke et al. | |
| 5,336,518 A | 8/1994 | Pallassana et al. | |
| 5,338,770 A | 8/1994 | Winters et al. | |
| 5,342,348 A | 8/1994 | Kaplan | |
| 5,342,387 A | 8/1994 | Summers | |
| 5,342,621 A | 8/1994 | Eury | |
| 5,354,257 A | 10/1994 | Roubin et al. | |
| 5,354,308 A | 10/1994 | Simon et al. | |
| 5,356,433 A | 10/1994 | Rowland et al. | |
| 5,366,504 A | 11/1994 | Andersen et al. | |
| 5,368,566 A | 11/1994 | Crocker | |
| 5,370,683 A | 12/1994 | Fontaine | |
| 5,370,691 A | 12/1994 | Samson | |
| 5,375,612 A | 12/1994 | Cottenceau et al. | |

| | | | | | |
|---|---|---|---|---|---|
| 5,376,112 A | 12/1994 | Duran | 5,591,224 A | 1/1997 | Schwartz et al. |
| 5,378,475 A | 1/1995 | Smith et al. ............... 424/473 | 5,591,227 A | 1/1997 | Dinh et al. |
| 5,380,299 A | 1/1995 | Fearnot et al. | 5,599,352 A | 2/1997 | Dinh et al. |
| 5,382,261 A | 1/1995 | Palmaz | 5,603,722 A | 2/1997 | Phan et al. |
| 5,383,853 A | 1/1995 | Jung et al. ............. 604/103.04 | 5,604,283 A | 2/1997 | Wada et al. ............... 524/236 |
| 5,383,928 A | 1/1995 | Scott et al. | 5,605,696 A | 2/1997 | Eury et al. |
| 5,387,235 A | 2/1995 | Chuter | 5,607,463 A | 3/1997 | Schwartz et al. |
| 5,389,106 A | 2/1995 | Tower | 5,607,475 A | 3/1997 | Cahalan et al. |
| 5,391,730 A | 2/1995 | Skotnicki et al. ........... 540/456 | 5,609,629 A | 3/1997 | Fearnot et al. |
| 5,393,772 A | 2/1995 | Yue et al. | 5,616,608 A | 4/1997 | Kinsella et al. ............. 514/449 |
| 5,395,390 A | 3/1995 | Simon et al. | 5,620,984 A | 4/1997 | Bianco et al. |
| 5,397,355 A | 3/1995 | Marin et al. | 5,621,102 A | 4/1997 | Bianco et al. |
| 5,399,352 A | 3/1995 | Hanson ...................... 424/423 | 5,622,975 A | 4/1997 | Singh et al. |
| 5,403,341 A | 4/1995 | Solar | 5,624,411 A | 4/1997 | Tuch |
| 5,405,377 A | 4/1995 | Cragg | 5,628,785 A | 5/1997 | Schwartz et al. |
| 5,409,696 A | 4/1995 | Narayanan et al. | 5,629,077 A | 5/1997 | Turnlund et al. |
| 5,411,549 A | 5/1995 | Peters | 5,629,315 A | 5/1997 | Bianco et al. |
| 5,415,619 A | 5/1995 | Lee et al. | 5,632,763 A | 5/1997 | Glastra |
| 5,417,969 A | 5/1995 | Hsu et al. ............... 424/78.27 | 5,632,771 A | 5/1997 | Boatman et al. ........... 623/1.15 |
| 5,419,760 A | 5/1995 | Narciso, Jr. | 5,632,776 A | 5/1997 | Kurumatani et al. ........ 424/423 |
| D359,802 S | 6/1995 | Fontaine | 5,632,840 A | 5/1997 | Campbell |
| 5,421,955 A | 6/1995 | Lau | 5,635,201 A | 6/1997 | Fabo ........................ 424/443 |
| 5,423,885 A | 6/1995 | Williams | 5,637,113 A | 6/1997 | Tartaglia et al. |
| 5,429,618 A | 7/1995 | Keogh | 5,643,312 A | 7/1997 | Fischell et al. |
| 5,429,634 A | 7/1995 | Narciso | 5,643,939 A | 7/1997 | Ohlstein |
| 5,439,446 A | 8/1995 | Barry | 5,646,160 A | 7/1997 | Morris et al. |
| 5,441,515 A | 8/1995 | Khosravi et al. | 5,648,357 A | 7/1997 | Bianco et al. |
| 5,441,516 A | 8/1995 | Wang et al. | 5,649,952 A | 7/1997 | Lam |
| 5,441,947 A | 8/1995 | Dodge et al. | 5,649,977 A | 7/1997 | Campbell |
| 5,443,458 A | 8/1995 | Eury | 5,651,174 A | 7/1997 | Schwartz et al. |
| 5,443,477 A | 8/1995 | Marin et al. | 5,652,243 A | 7/1997 | Bianco et al. |
| 5,443,496 A | 8/1995 | Schwartz et al. | 5,653,747 A | 8/1997 | Dereume ................... 623/1.54 |
| 5,443,498 A | 8/1995 | Fontaine | 5,653,992 A | 8/1997 | Bezwada et al. |
| 5,443,500 A | 8/1995 | Sigwart | 5,662,609 A | 9/1997 | Slepian |
| 5,447,724 A | 9/1995 | Heimus et al. | 5,665,591 A | 9/1997 | Sonenshein et al. ........ 435/375 |
| 5,449,372 A | 9/1995 | Schmaltz et al. | 5,665,728 A | 9/1997 | Morris et al. |
| 5,449,373 A | 9/1995 | Pinchasik et al. | 5,667,764 A | 9/1997 | Kopia et al. ............... 424/1.45 |
| 5,449,382 A | 9/1995 | Dayton | 5,669,924 A | 9/1997 | Shaknovich |
| 5,464,450 A | 11/1995 | Buscemi et al. | 5,670,506 A | 9/1997 | Leigh et al. |
| 5,464,540 A | 11/1995 | Friesen et al. ............... 210/640 | 5,672,638 A | 9/1997 | Verhoeven et al. ......... 523/112 |
| 5,464,650 A | 11/1995 | Berg et al. | 5,674,242 A | 10/1997 | Phan et al. ................ 606/198 |
| 5,474,563 A | 12/1995 | Myler et al. ............... 606/108 | 5,679,400 A | 10/1997 | Tuch |
| 5,486,357 A | 1/1996 | Narayanan | 5,679,659 A | 10/1997 | Verhoeven et al. |
| 5,496,365 A | 3/1996 | Sgro | 5,684,061 A | 11/1997 | Ohnishi et al. ............. 523/114 |
| 5,500,013 A | 3/1996 | Buscemi et al. | 5,691,311 A | 11/1997 | Maraganore et al. ......... 514/12 |
| 5,504,091 A | 4/1996 | Molnar-Kimber et al. .. 514/291 | 5,693,085 A | 12/1997 | Buirge et al. |
| 5,510,077 A | 4/1996 | Dinh et al. | 5,697,967 A | 12/1997 | Dinh et al. |
| 5,512,055 A | 4/1996 | Domb et al. ............... 604/265 | 5,697,971 A | 12/1997 | Fischell et al. |
| 5,516,781 A | 5/1996 | Morris et al. | 5,700,286 A | 12/1997 | Tartaglia et al. |
| 5,519,042 A | 5/1996 | Morris et al. ............... 514/378 | 5,707,385 A | 1/1998 | Williams |
| 5,523,092 A | 6/1996 | Hanson et al. | 5,709,874 A | 1/1998 | Hanson et al. |
| 5,527,354 A | 6/1996 | Fontaine et al. | 5,713,949 A | 2/1998 | Jayaraman ................. 623/1.12 |
| 5,545,208 A | 8/1996 | Wolff et al. | 5,716,981 A | 2/1998 | Hunter et al. ............... 514/449 |
| 5,551,954 A | 9/1996 | Buscemi et al. | 5,725,549 A | 3/1998 | Lam |
| 5,554,182 A | 9/1996 | Dinh et al. | 5,725,567 A | 3/1998 | Wolff et al. |
| 5,554,954 A | 9/1996 | Takahashi | 5,728,150 A | 3/1998 | McDonald et al. |
| 5,556,413 A | 9/1996 | Lam | 5,728,420 A | 3/1998 | Keogh |
| 5,559,122 A | 9/1996 | Nelson et al. ............... 514/291 | 5,731,326 A | 3/1998 | Hart et al. |
| 5,562,922 A | 10/1996 | Lambert | 5,733,327 A | 3/1998 | Igaki et al. |
| 5,563,146 A | 10/1996 | Morris et al. | 5,733,920 A | 3/1998 | Mansuri et al. |
| 5,569,197 A | 10/1996 | Helmus et al. | 5,733,925 A | 3/1998 | Kunz et al. |
| 5,569,295 A | 10/1996 | Lam | 5,735,897 A | 4/1998 | Buirge |
| 5,569,462 A | 10/1996 | Martinson et al. ........... 424/423 | 5,739,138 A | 4/1998 | Bianco et al. |
| 5,569,463 A | 10/1996 | Helmus et al. ............. 424/426 | 5,755,734 A | 5/1998 | Richter et al. |
| 5,571,089 A | 11/1996 | Crocker ................ 604/103.01 | 5,755,772 A | 5/1998 | Evans et al. ............... 128/898 |
| 5,571,166 A | 11/1996 | Dinh et al. | 5,759,205 A | 6/1998 | Valentini .................... 433/173 |
| 5,574,059 A | 11/1996 | Regunathan et al. | 5,769,883 A | 6/1998 | Buscemi et al. |
| 5,575,818 A | 11/1996 | Pinchuk ..................... 623/1.15 | 5,776,184 A | 7/1998 | Tuch |
| 5,578,075 A | 11/1996 | Dayton | 5,780,462 A | 7/1998 | Lee et al. ................... 514/183 |
| 5,580,873 A | 12/1996 | Bianco et al. | 5,780,476 A | 7/1998 | Underiner et al. |
| 5,580,874 A | 12/1996 | Bianco et al. | 5,782,908 A | 7/1998 | Cahalan et al. |
| 5,591,140 A | 1/1997 | Narayanan et al. | 5,788,979 A | 8/1998 | Alt |
| 5,591,197 A | 1/1997 | Orth et al. | 5,792,106 A | 8/1998 | Mische .................. 604/103.01 |

| | | |
|---|---|---|
| 5,792,772 A | 8/1998 | Bianco et al. |
| 5,798,372 A | 8/1998 | Davies et al. |
| 5,799,384 A | 9/1998 | Schwartz et al. |
| 5,800,507 A | 9/1998 | Schwartz |
| 5,800,508 A | 9/1998 | Goicoechea et al. |
| 5,807,861 A | 9/1998 | Klein et al. |
| 5,811,447 A | 9/1998 | Kunz et al. |
| 5,820,917 A | 10/1998 | Tuch |
| 5,820,918 A | 10/1998 | Ronan et al. |
| 5,824,048 A | 10/1998 | Tuch |
| 5,824,049 A | 10/1998 | Ragheb et al. |
| 5,827,587 A | 10/1998 | Fukushi ............... 428/36.6 |
| 5,833,651 A | 11/1998 | Donovan et al. |
| 5,837,008 A | 11/1998 | Berg et al. |
| 5,837,313 A | 11/1998 | Ding et al. |
| 5,843,120 A | 12/1998 | Israel et al. ............. 623/1.15 |
| 5,843,166 A | 12/1998 | Lentz et al. ............. 623/1.13 |
| 5,843,172 A | 12/1998 | Yan |
| 5,849,034 A | 12/1998 | Schwartz |
| 5,851,217 A | 12/1998 | Wolff et al. |
| 5,851,231 A | 12/1998 | Wolff et al. |
| 5,858,990 A | 1/1999 | Walsh |
| 5,861,027 A | 1/1999 | Trapp |
| 5,865,814 A | 2/1999 | Tuch |
| 5,871,535 A | 2/1999 | Wolff et al. |
| 5,873,904 A | 2/1999 | Ragheb et al. |
| 5,876,433 A | 3/1999 | Lunn |
| 5,877,224 A | 3/1999 | Brocchini et al. ....... 514/772.2 |
| 5,879,697 A | 3/1999 | Ding et al. |
| 5,882,335 A | 3/1999 | Leone et al. |
| 5,891,108 A | 4/1999 | Leone et al. |
| 5,893,840 A | 4/1999 | Hull et al. ............. 604/103.02 |
| 5,897,911 A | 4/1999 | Loeffler ............... 427/2.25 |
| 5,900,246 A | 5/1999 | Lambert |
| 5,902,266 A | 5/1999 | Leone et al. |
| 5,912,253 A | 6/1999 | Cottens et al. ............. 514/291 |
| 5,916,910 A | 6/1999 | Lai ...................... 514/423 |
| 5,922,393 A | 7/1999 | Jayaraman ............... 427/2.3 |
| 5,922,730 A | 7/1999 | Hu et al. ................. 514/291 |
| 5,932,243 A | 8/1999 | Fricker et al. ............. 424/450 |
| 5,932,299 A | 8/1999 | Katoot ................... 427/508 |
| 5,932,580 A | 8/1999 | Levitzki et al. ............. 181/152 |
| 5,951,586 A | 9/1999 | Berg et al. |
| 5,957,971 A | 9/1999 | Schwartz |
| 5,968,091 A | 10/1999 | Pinchuk et al. ............ 623/1.16 |
| 5,972,027 A | 10/1999 | Johnson |
| 5,976,534 A | 11/1999 | Hart et al. |
| 5,977,163 A | 11/1999 | Li et al. |
| 5,980,553 A | 11/1999 | Gray et al. |
| 5,980,566 A | 11/1999 | Alt et al. |
| 5,980,972 A | 11/1999 | Ding |
| 5,981,568 A | 11/1999 | Kunz et al. |
| 5,985,307 A | 11/1999 | Hanson et al. |
| 5,997,468 A | 12/1999 | Wolff et al. |
| 6,004,346 A | 12/1999 | Wolff et al. |
| 6,015,432 A | 1/2000 | Rakos et al. ............. 623/1.13 |
| 6,015,815 A | 1/2000 | Mollison ................ 514/291 |
| 6,039,721 A | 3/2000 | Johnson et al. |
| 6,059,813 A | 5/2000 | Vrba et al. |
| 6,071,305 A | 6/2000 | Brown et al. |
| 6,074,659 A | 6/2000 | Kunz et al. |
| 6,080,190 A | 6/2000 | Schwartz |
| 6,096,070 A | 8/2000 | Ragheb et al. |
| 6,120,536 A | 9/2000 | Dinge et al. |
| 6,120,847 A | 9/2000 | Yang et al. ................ 427/335 |
| 6,136,798 A | 10/2000 | Cody et al. |
| 6,140,127 A | 10/2000 | Sprague |
| 6,146,358 A | 11/2000 | Rowe |
| 6,153,252 A | 11/2000 | Hossainy et al. |
| 6,159,488 A | 12/2000 | Nagier et al. ............. 424/423 |
| 6,171,232 B1 | 1/2001 | Papandreou et al. |
| 6,171,609 B1 | 1/2001 | Kunz |
| 6,177,272 B1 | 1/2001 | Nabel et al. |
| 6,179,817 B1 | 1/2001 | Zhong ................... 604/265 |
| 6,187,757 B1 | 2/2001 | Clackson et al. ............. 514/31 |
| 6,193,746 B1 | 2/2001 | Strecker ................. 623/1.13 |
| 6,214,901 B1 | 4/2001 | Chudzik et al. |
| 6,225,346 B1 | 5/2001 | Tang et al. ................ 514/523 |
| 6,240,616 B1 | 6/2001 | Yan |
| 6,245,537 B1 | 6/2001 | Williams et al. ............. 435/135 |
| 6,251,920 B1 | 6/2001 | Grainger et al. ............. 514/319 |
| 6,254,632 B1 | 7/2001 | Wu et al. |
| 6,254,634 B1 | 7/2001 | Anderson et al. .......... 623/1.42 |
| 6,258,121 B1 | 7/2001 | Yang et al. |
| 6,268,390 B1 | 7/2001 | Kunz |
| 6,273,913 B1 | 8/2001 | Wright et al. |
| 6,284,305 B1 | 9/2001 | Ding et al. ................. 427/2.28 |
| 6,287,320 B1 | 9/2001 | Slepian |
| 6,287,628 B1 | 9/2001 | Hossainy et al. |
| 6,299,604 B1 | 10/2001 | Ragheb et al. |
| 6,306,144 B1 | 10/2001 | Sydney et al. .............. 606/108 |
| 6,306,166 B1 | 10/2001 | Barry et al. |
| 6,306,176 B1 | 10/2001 | Whitbourne |
| 6,306,421 B1 | 10/2001 | Kunz et al. |
| 6,309,380 B1 | 10/2001 | Larson et al. |
| 6,309,660 B1 | 10/2001 | Hsu et al. |
| 6,313,264 B1 | 11/2001 | Caggiano et al. |
| 6,316,018 B1 | 11/2001 | Ding et al. ................. 424/423 |
| 6,335,029 B1 | 1/2002 | Kamath et al. ............. 424/423 |
| 6,358,556 B1 | 3/2002 | Ding et al. ................. 427/2.24 |
| 6,369,039 B1 | 4/2002 | Palasis et al. .............. 424/93.2 |
| 6,379,382 B1 | 4/2002 | Yang ................... 623/1.42 |
| 6,387,121 B1 | 5/2002 | Alt ..................... 623/1.15 |
| 6,403,635 B1 | 6/2002 | Kinsella et al. ............. 514/449 |
| 6,407,067 B1 | 6/2002 | Schafer .................. 514/19 |
| 6,517,858 B1 | 2/2003 | Le Moel et al. ............. 424/424 |
| 6,517,889 B1 | 2/2003 | Jayaraman ................ 427/2.24 |
| 6,545,097 B2 | 4/2003 | Pinchuk et al. ............. 525/240 |
| 6,585,764 B2 | 7/2003 | Wright et al. ............. 623/1.42 |
| 6,620,194 B2 | 9/2003 | Ding et al. ................. 623/1.43 |
| 6,746,773 B2 | 6/2004 | Llanos et al. ............. 428/421 |
| 6,776,796 B2 | 8/2004 | Falotico et al. ............. 623/1.46 |
| 6,808,536 B2 | 10/2004 | Wright et al. ............. 623/1.42 |
| 2001/0007083 A1 | 7/2001 | Roorda |
| 2001/0029351 A1 | 10/2001 | Falotico et al. ........ 604/103.02 |
| 2001/0029660 A1 | 10/2001 | Johnson |
| 2001/0032014 A1 | 10/2001 | Yang et al. |
| 2001/0034363 A1 | 10/2001 | Li et al. |
| 2001/0037145 A1 | 11/2001 | Guruwaiya et al. |
| 2002/0010418 A1 | 1/2002 | Lary et al. ............. 604/101.04 |
| 2002/0032477 A1 | 3/2002 | Helmus et al. .............. 623/1.2 |
| 2002/0041899 A1 | 4/2002 | Chudzik et al. ............. 424/487 |
| 2002/0061326 A1 | 5/2002 | Li et al. .................... 424/424 |
| 2002/0068969 A1 | 6/2002 | Shanley et al. ............. 623/1.16 |
| 2002/0071902 A1 | 6/2002 | Ding et al. ................. 427/2.24 |
| 2002/0082680 A1 | 6/2002 | Shanley et al. ............. 623/1.16 |
| 2002/0082685 A1 | 6/2002 | Sirhan et al. ............. 623/1.42 |
| 2002/0091433 A1 | 7/2002 | Ding et al. ................. 623/1.2 |
| 2002/0095114 A1 | 7/2002 | Palasis .................. 604/96.01 |
| 2002/0099438 A1 | 7/2002 | Furst .................... 623/1.16 |
| 2002/0103526 A1 | 8/2002 | Steinke .................. 623/1.11 |
| 2002/0119178 A1 | 8/2002 | Levesque et al. ............. 424/423 |
| 2002/0123505 A1 | 9/2002 | Mollison et al. ............. 514/291 |
| 2002/0127327 A1 | 9/2002 | Schwartz et al. ............ 427/2.15 |
| 2002/0133222 A1 | 9/2002 | Das ..................... 623/1.16 |
| 2002/0133224 A1 | 9/2002 | Bajgar et al. ............. 623/1.39 |
| 2002/0165608 A1 | 11/2002 | Llanos ................... 604/500 |
| 2002/0193475 A1 | 12/2002 | Hossainy et al. ............ 524/113 |
| 2003/0065377 A1 | 4/2003 | Davila et al. ............. 604/265 |
| 2003/0216699 A1 | 11/2003 | Falotico |
| 2004/0049265 A1 | 3/2004 | Ding et al. ................. 623/1.42 |
| 2004/0243097 A1 | 12/2004 | Falotico et al. ............. 604/500 |
| 2004/0260268 A1 | 12/2004 | Falotico et al. ............. 604/500 |
| 2005/0002986 A1 | 1/2005 | Falotico et al. ............. 424/426 |
| 2005/0004663 A1 | 1/2005 | Llanos et al. ............. 623/1.46 |
| 2005/0033261 A1 | 2/2005 | Falotico et al. ............. 604/500 |

| | | | |
|---|---|---|---|
| 2005/0106210 A1 | 5/2005 | Ding et al. | 424/423 |
| 2005/0187611 A1 | 8/2005 | Ding et al. | 623/1.15 |
| 2005/0208200 A1 | 9/2005 | Ding et al. | 427/2.25 |
| 2006/0088654 A1 | 4/2006 | Ding et al. | 427/2.21 |
| 2006/0089705 A1 | 4/2006 | Ding et al. | 623/1.15 |

FOREIGN PATENT DOCUMENTS

| | | |
|---|---|---|
| DE | 19723723 A1 | 12/1998 |
| EP | 0 145 166 A2 | 6/1985 |
| EP | 0 177 330 A2 | 4/1986 |
| EP | 0 183 372 A1 | 6/1986 |
| EP | 0 221 570 A2 | 5/1987 |
| EP | 0 421 729 A2 | 4/1991 |
| EP | 0 540 290 A2 | 10/1992 |
| EP | 0 568 310 A1 | 11/1993 |
| EP | 0 604 022 A1 | 6/1994 |
| EP | 0 621 015 A1 | 10/1994 |
| EP | 0 623 354 A1 | 11/1994 |
| EP | 0 734 698 A2 | 3/1996 |
| EP | 0 712 615 A1 | 5/1996 |
| EP | 0 716 836 A1 | 6/1996 |
| EP | 0 800 801 A1 | 8/1996 |
| EP | 0 734 721 A1 | 10/1996 |
| EP | 0 747 069 A2 | 12/1996 |
| EP | 0 761 251 A1 | 3/1997 |
| EP | 0 830 853 A1 | 7/1997 |
| EP | 0 540 290 B1 | 1/1998 |
| EP | 0 815 803 A1 | 7/1998 |
| EP | 0 850 651 A2 | 7/1998 |
| EP | 0 938 878 A3 | 9/1999 |
| EP | 0950386 B1 | 10/1999 |
| EP | 0 968 688 A1 | 1/2000 |
| EP | 0 633 032 B1 | 2/2001 |
| EP | 1 192 957 A2 | 4/2002 |
| EP | 1 588 726 A1 | 10/2005 |
| EP | 1 588 727 A1 | 10/2005 |
| FR | 0 566 807 A1 | 4/1992 |
| GB | 1 205 743 | 9/1970 |
| GB | 2 135 585 A | 9/1984 |
| GB | 0 662 307 A2 | 12/1994 |
| SU | 660689 | 5/1979 |
| SU | 1457921 | 2/1989 |
| WO | 89/03232 A1 | 4/1989 |
| WO | WO 91/12779 A1 | 9/1991 |
| WO | WO 92/15286 A1 | 9/1992 |
| WO | WO 94/01056 A1 | 1/1994 |
| WO | WO 94/21308 A1 | 9/1994 |
| WO | WO 94/21309 A1 | 9/1994 |
| WO | WO 94/24961 A1 | 11/1994 |
| WO | WO 96/00272 A1 | 1/1996 |
| WO | WO 96/26689 A1 | 9/1996 |
| WO | WO 96/32907 A1 | 10/1996 |
| WO | WO 96/34580 A1 | 11/1996 |
| WO | 96/41807 A1 | 12/1996 |
| WO | WO 97/25000 A1 | 7/1997 |
| WO | WO 97/33534 A1 | 9/1997 |
| WO | 97/35575 A1 | 10/1997 |
| WO | 98/08463 A1 | 3/1998 |
| WO | WO 98/13344 A1 | 4/1998 |
| WO | WO 98/19628 A1 | 5/1998 |
| WO | 98/23244 A1 | 6/1998 |
| WO | WO 98/23228 A1 | 6/1998 |
| WO | WO 98/34669 A1 | 8/1998 |
| WO | WO 98/36784 A1 | 8/1998 |
| WO | WO 98/47447 A1 | 10/1998 |
| WO | WO 98/56312 A1 | 12/1998 |
| WO | 00/21584 A1 | 4/2000 |
| WO | 00/27455 A1 | 5/2000 |
| WO | WO 00/27445 A1 | 5/2000 |
| WO | 00/32255 A1 | 6/2000 |
| WO | 00/38754 A1 | 7/2000 |
| WO | 01/87342 A2 | 11/2001 |
| WO | 01/87372 A1 | 11/2001 |
| WO | 01/87373 A1 | 11/2001 |
| WO | WO 01/87376 A1 | 11/2001 |
| WO | 02/26139 A1 | 4/2002 |
| WO | 02/26271 A1 | 4/2002 |
| WO | 02/26280 A1 | 4/2002 |
| WO | 02/26281 A1 | 4/2002 |
| WO | 03/015664 A1 | 2/2003 |
| WO | 03/057218 A1 | 7/2003 |

OTHER PUBLICATIONS

U.S. Appl. No. 07/819,314, filed Jan. 9, 1992, Morris.
U.S. Appl. No. 08/424,884, filed Apr. 19, 1995, Helmus et al.
U.S. Appl. No. 08/526,273, filed Sep. 11, 1995, Ding.
U.S. Appl. No. 08/730,542, filed Oct. 11, 1996, Helmus.
U.S. Appl. No. 09/575,480, filed May 19, 2000, Kopia.
U.S. Appl. No. 10/431,059, filed May 7, 2003, Falotico.
Abraham, R. T., "Mammalian target of rapamycin: Immunosupressive drugs offer new insight into cell growth regulation," *Progress in Inflammation Research*, 2000, Switzerland.
Alvarado, R. et al., "Evaluation of Polymer-coated Balloon-expandable Stents in Bile Ducts," *Radiology*, 1989, 170, 975-978.
Badimon, J. J. et al., "Inhibitory Effects of Rapamycin on Intimal Hyperplasia After PTCA," *JACC*, Mar. 1998.
Bailey et al., "Polymer Coating of Palmaz-Schatz Stent Attenuates Vascular Spasm after Stent Placement," *Circulation*, 82:III-541 (1990).
Berk, B. C. et al., "Pharmacologic Roles of Heparin and Glucocorticoids to Prevent Restenosis After Coronary Angioplasty," *JACC*, May 1991, 17(6), 111B-117B.
Bertram, P. G. et al., "The 14-3-3 proteins positively regulate rapamycin-sensitive signaling," *Current Biology*, 1998, 8, 1259-1267.
Biomaterials Science (B.D. Ratner, Ed.), Academic Press, New York, NY, pp. 228-238, 1996.
Campbell, G. R. et al., "Phenotypic Modulation of Smooth Muscle Cells in Primary Culture, Vascular Smooth Muscle Cells in Culture," *CRC Press*, 1987, 39-55.
Chang, M. W. et al., "Adenovirus-mediated Over-expression of the Cyclin/Cyclin-dependent Kinase inhibitor, p21 inhibits Vascular Smooth Muscle Cell Proliferation and Neointima Formation in the Rat Carotid Artery Model of Balloon Angioplasty," *J. Clin. Invest.*, 1995, 96, 2260-2268.
Chung, J. et al., "Rapamycin-FKBP specifically blocks growth-dependent activation of and signaling by the 70 kd S6 protein kinases," *Cell*, Jun. 26, 1992, 69(7), 1227-1236.
Clowes, A. W. et al., "Kinetics of cellular proliferation after arterial injury. IV. Heparin inhibits rat smooth muscle mitogenesis and migration," *Circ. Res.*, 1986, 58(6), 839-845.
Clowes, A. W. et al., Kinetics of Cellular Proliferation after Arterial Injury, *Laboratory Investigation*, 1985, 52(6), 611-616.
Clowes, A. W. et al., "Significance of quiescent smooth muscle migration in the injured rat carotid artery," *Circ Res.* 1985, 56(1), 139-145.
Clowes, A. W., "Suppression by heparin of smooth muscle cell proliferation in injured arteries," *Nature*, 1977, 265(5595), 625-626.
Colburn, M. D. et al., "Dose responsive suppression of myointimal hyperplasia by dexamethasone," *J. Vasc. Surg.*, 1992, 15, 510-518.
Currier, J. W. et al., "Colchicine Inhibits Restenosis After Iliac Angioplasty in the Atherosclerotic Rabbit," *Circ.*, 1989, 80(4), 11-66 (Abstract No. 0263).
Encyclopedia of Polymer Science and Engineering, vol. 7, Fluocarbon Elastomers, p. 257-267, Mar. 1989.
Farb, A. et al., "Vascular smooth muscle cell cytotoxicity and sustained inhibition of neointimal formation by fibroblast growth factor 2-saporin fusion protein," *Circ. Res.*, 1997, 80, 542-550.
Ferns, G. A. A. et al., "Inhibition of Neointimal Smooth Muscle Accumulation After Angioplasty by an Antibody to PDGF," *Science*, 1991, 253, 1129-1132.

Fischman, D. L. et al., "A Randomized Comparison of Coronary-Stent Placement and Balloon Angioplasty in the Treatment of Coronary Artery Disease," *N. Eng. J. Med.*, Aug. 25, 1994, 331(8), 496-501.

Franklin, S. M. et al., "Pharmacologic prevention of restenosis after coronary angioplasty: review of the randomized clinical trials," *Coronary Artery Disease* Mar. 1993, 4(3), 232-242.

Fukuyama, J. et al., "Tranilast suppresses the vascular intimal hyperplasia after balloon injury in rabbits fed on a high-cholesterol diet," *Eur. J. Pharmacol.*, 1996, 318, 327-332.

Gregory, C. R. et al., "Rapamycin Inhibits Arterial Intimal Thickening Caused by Both Alloimmune and Mechanical Injury," *Transplantation*, Jun. 1993, 55(6), 1409-1418.

Gregory, C. R. et al, "Treatment with Rapamycin and Mycophenolic Acid Reduces Arterial Intimal Thickening Produced by Mechanical Injury and Allows Endothelial Replacement," *Transplantation*, Mar. 15, 1995, 59(5), 655-661.

Guyton, J. R. et al., "Inhibition of rat arterial smooth muscle cell proliferation by heparin. In vivo studies with anticoagulant and nonanticoagulant heparin," *Circ. Res.*, 1980, 46, 625-634.

Hansson, G. K. et al., "Interferon-$\gamma$ Inhibits Arterial Stenosis After Injury," *Circ.*, 1991, 84, 1266-1272.

Hashemolhosseini, S. et al., "Rapamycin Inhibition of the G1 to S Transition Is Mediated by Effects on Cyclin D1 mRNA and Protein Stability," *J. Biol Chem*, Jun. 5, 1998, 273, 14424-14429.

Jonasson, J. et al., "Cyclosporin A inhibits smooth muscle proliferation in the vascular response to injury," *Proc. Natl., Acad. Sci.*, 1988, 85, 2303-2306.

Kuhnt, M. et al., "Microbial Conversion of Rapamycin," *Enzyme and Microbial Technology*, 1997, 21, 405-412.

Lange, R. A. MD et al., "Restenosis After Coronary Balloon Angioplasty," *Annu. Rev. Med.*, 1991, 42, 127-132.

Liu, M. W. et al., "Trapidil in Preventing Restenosis After Balloon Angioplasty in the Atherosclerotic Rabbit," *Circ.*, 1990, 81, 1089-1093.

Liu, M. W., MD et al., "Restenosis After Coronary Angioplasty Potential Biologic Determinants and Role of Intimal Hyperplasia," *Circulation*, 1989, 79, 1374-1387.

Lundergan, C. F. et al., "Peptide inhibition of Myointimal Proliferation by Angiopeptin, a Somatostatin Analogue," *JACC*, May 1991, 17(6), 132B-136B.

Majesky, M. W. et al., "Heparin regulates smooth muscle S phase entry in the injured rat carotid artery," *Circ. Res.*, 1987, 61, 296-300.

Marx, S. O. et al., "Rapamycin-FKBP Inhibits Cell Cycle Regulators of Proliferation in Vascular Smooth Muscle Cells," *Circ. Res.*, 1995, 76, 412-417.

Nemecek, G. M. et al., "Terbinafine Inhibits the Mitogenic Response to Platelet-Derived Growth Factor in Vitro and Neoinimal Proliferation in Vivo," *J. Pharmacol. Exp. Thera.*, 1989, 248, 1167-1174.

Okada, T. et al., "Localized Release of Perivascular Heparin Inhibits Intimal Proliferation after Endothelial Injury without Systemic Anticoagulation," *Neurosurgery*, 1989, 25, 892-898.

Poon, M. et al., "Rapamycin Inhibits Vascular Smooth Muscle Cell Migration," *J. Clin Invest.*, Nov. 1996, 98(10), 2277-2283.

Popma, J. J. et al., "Clinical trials of restenosis after coronary angioplasty," *Circulation*, Sep. 1991, 84(3), 1426-1436.

Powell, J. S. et al., "Inhibitors of Angiotensin-Converting Enzyme Prevent Myointimal Proliferation After Vascular Injury," *Science*, 1989, 245, 186-188.

Rensing, B. J. et al., Coronary restenosis elimination with a sirolimus eluting stent, *European Heart Journal*, 2001, 22, 2125-2130.

Rodeck, C. et al., "Methods for the Transcervical Collection of Fetal Cells During the First Trimester of Pregnancy," *Prenatal Diagnosis*, 1995, 15, 933-942.

Serruys, P. W. et al., "A comparison of balloon-expandable-stent implantation with balloon angioplasty in patients with coronary artery disease," *N Engl J Med*, Aug. 25, 1994; 331(8), 489-495.

Serruys, P. W. et al., "Evaluation of ketanserin in the prevention of restenosis after percutaneous transluminal coronary angioplasty. A multicenter randomized double-blind placebo-controlled trial," *Circulation*. Oct. 1993; 88(4 Pt 1), 1588-1601.

Serruys, P. W. et al., "Heparin-coated Palmaz-Schatz stents in human coronary arteries. Early outcome of the Benestent-II Pilot Study," *Circulation*, Feb. 1, 1996; 93(3), 412-422.

Siekierka, J. J., "Probing T-Cell Signal Transduction Pathways with the Immunosupressive Drugs, FK-506 and Rapamycin," *Immunologic Research*, 1994, 13, 110-116.

Sigwart, et al., "Intravascular Stents to Prevent Occlusion and Restenosis After Transluminal Angioplasty," *N. Engl. J. Med.*, Mar. 19, 1987, 316, 701-706.

Simons, M. et al., "Antisense c-*myb* oligonucleotides inhibit intimal arterial smooth muscle cell accumulation in vivo," *Nature*, 1992, 359, 67-70.

Snow, A. D. et al., "Heparin modulates the composition of the extracellular matrix domain surrounding arterial smooth muscle cells," *Am. J. Pathol.*, 1990, 137, 313-330.

Sollott, S. J. et al., "Taxol Inhibits Neointimal Smooth Muscle Cell Accumulation after Angioplasty in the Rat," *J. Clin. Invest.*, 1995, 95, 1869-1876.

van Der Giessen, et al., "Self-expandable Mesh Stents: an Experimental Study Comparing Polymer Coated and Uncoated Wallstent Stents in the Coronary Circulation of Pigs," *Circulation* 1990, 82(suppl. III):III-542.

van Der Giessen, W. J. et al., "Coronary stenting with polymer-coated and uncoated self-expanding endoprostheses in pigs," Coron. Art. Disease 1992; 3, 631-640.

Vasey, C. G. et a., "Clinical Cardiology: Stress Echo and Coronary Flow", , *Circulation*, Oct. 1989, 80(4) Supplement II, II-66.

Verweire, E. et al., "Evaluation of Fluorinated Polymers As Coronary Stent Coating," *Journal of Materials Science: Materials in medicine*, Apr. 2000.

Weinberger, J. et al., "Intracoronary irradiation: dose response for the prevention of restenosis in swine," *Int. J. Rad. Onc. Biol. Phys.*, 1996, 36, 767-775.

Preliminary Amendment in U.S. Appl. No. 07/258,189, May 22, 1989.

Trial Transcript from Nov. 6, 2000 at 185-90 and 235-36 (Attorney's opening remarks regarding '984 patent).

Trial Transcript from Nov. 7, 2000 at 274-301, 307-315, 320-28 and 332 (Cordis expert testimony regarding the Palmaz-Schatz stent); 370-379, 480-496 (J. Palmaz testimony regarding the Palmaz-Schatz stent, the '984 patent and the connected z-stent art).

Trial Transcript from Nov. 8, 2000 at 547-63, 657-63, 674-722, 782-85 (Cordis expert testimony regarding the Palmaz-Schatz stent, the '984 patent and the connected z-stent art).

Trial Transcript from Nov. 9, 2000 at 819-23, 921 (Cordis expert testimony regarding the '984 patent); 926-941 . (R. Croce testimony re Palmaz-Schatz stent); 1033-1053. (R. Schatz testimony).

Trial Transcript from Nov. 13, 2000 at 1086-1134. (R. Schatz testimony); 1275-1305 (Cordis expert testimony regarding the '984 patent).

Trial Transcript from Nov. 14, 2000 at 1390-1404, 1448-1454, 1486-1500 (Cordis expert testimony regarding the '984 patent).

Trial Transcript from Nov. 15, 2000 at 1686-87, 1724-42, 1828-34, 1850-54, 1887-92 (AVE expert testimony regarding the '984 patent).

Trial Transcript from Nov. 16, 2000 at 2077-198 (AVE expert testimony regarding the alleged obviousness of the '984 patent).

Trial Transcript from Nov. 17, 2000 at 2331-34 (jury instructions as to the meaning of the limitations of the claims of the '984 patent).

Trial Transcript from Nov. 20, 2000 at 2441-48, 2499-2500, 2546-50, 2552-56 (Attorney's closing arguments regarding the '984 patent).

Trial Transcript from Nov. 21, 2000 at 2592-94 (reading of jury verdict).

Trial Transcript from Dec. 18, 2000 at 2750-95 (Cordis expert testimony regarding the Palmaz-Schatz stent during the damages phase).

Trial Transcript from Dec. 20, 2000 at 3421-88 (AVE expert testimony regarding the Palmaz-Schatz stent during the damages phase).

Jury verdict, dated Nov. 21, 2000.

District Court decisions on post-trial motions (194 F. Supp. 2d 323).

Court of Appeal for the Federal Circuit decision (339 F.3d 1352).

Trial Transcript from Mar. 4, 2005 at 133-135, 171-173 and 192-96 (Attorney's opening remarks regarding '984 validity).
Trial Transcript from Mar. 7, 2005 at 275-31 1 (Cordis expert testimony regarding the Palmaz-Schatz stent); 342-46, 353-59, 416-425 (J. Palmaz testimony regarding the Palmaz-Schatz stent, the '984 patent and the connected z-stent art); 430-449, 452-58, 462-492 (R. Croce testimony regarding the Palmaz-Schatz stent); 500-507 (Cordis expert testimony regarding the '984 patent).
Trial Transcript from Mar. 8, 2005 at 609 (Cordis expert testimony regarding the '984 patent); 628-73, 724-740, 773, 801-839 (Cordis expert testimony regarding the '984 patent, the prior art and the Palmaz-Schatz stent).
Trial Transcript from Mar. 9, 2005 at 936-49, 968-69 (Cordis expert testimony regarding the '984 patent, the prior art and the Palmaz-Schatz stent).
Trial Transcript from Mar. 10, 2005 at 1427-74, 178-1509, 1514-23 (AVE expert testimony regarding the alleged obviousness of the '984 patent); 1566-93 (AVE expert testimony regarding Palmaz-Schatz stent); 1634-49 (R. Schatz testimony).
Trial Transcript from Mar. 11, 2005 at 1846-47, 1891-1900, 1919 (Attorneys' closing arguments regarding '984 obviousness).
Trial Transcript from Mar. 14, 2005 at 1964-67 (reading of jury verdict).
Jury verdict dated Mar. 14, 2005.
Medtronic Vascular Inc.'s Opening Brief in Support of Its Motion for Judgment As A Infringement Claim dated Apr. 19, 2005.
Medtronic Vascular Inc.'s Opening Brief in Support of Its Motion for a New Trial dated Apr. 19, 2005.
D.I. 1407, Cordis' Combined Answering Brief In Opposition to AVE's Motion for JMOL on Infringement of the Palmaz '762 and Schatz '984 Patents and Its Motion for a New Trial dated May 5, 2005.
D.I. 1414, Medtronic Vascular Inc.'s Combined Reply Brief In Support of Its Motion for Judgment as a Matter of Law on Cordis Corp.'s Patent Infringement Claims and Its Motion for a New Trial dated May 19, 2005.
Trial Transcript from Feb. 8, 2001 at 372-412, 449-469 (B. Tobor testimony regarding the prosecution of the '417, '984 and '332 patents); 510-13 (J. Milnamow testimony regarding the prosecution of the '332 patent); 558-604 (J. Palmaz testimony regarding the prosecution of the '417, '984 and '332 patents and the prior art).
Trial Transcript from Feb. 9, 2001 at 637-45, 662-672, 682-85 (J. Palmaz testimony regarding the prior art); 699-742 (R. Schatz testimony); 769-770, 790-95 (Cordis expert testimony regarding prior art).
D.I. 1067, Medtronic AVE, Inc.'s Post-Trial Brief Relating to the Unenforceability of the '762 and '984 Patents Due to Inequitable Conduct.
D.I. 1077, Cordis' Combined Answering Brief in Opposition to AVE's BSC's Post-Hearing Briefs on Alleged Inequitable Conduct Concerning the '762, '984 and '332 Patents.
D.I. 1089, Reply Brief In Support of Medtronic AVE, Inc.'s Contention that the '762 and '984 Patents are Unenforceable Due to Inequitable Conduct dated May 7, 2001.
C.A. No. 00-886-SLR, Answer and Counterclaims of Def. Medtronic AVE, Inc. To First Amended Complaint of Plaintiff Cordis Corp.
BSC's Opening Post-Trial Brief in Support of Its Defense That the Patents in Suit Are Unenforceable, dated Mar. 16, 2001.
Reply Brief in Support of BSC's Defense That the Patents in Suit Are Unenforceable, dated May 7, 2001.
Court's Decision on allegations of inequitable conduct (194 F. Supp. 2d 323) Mar. 28, 2002.
Trial Transcript from Nov. 21, 2000 at 155-57 and 180-84 (Attorneys'opening remarks regarding '332 patent).
Trial Transcript from Nov. 27, 2000 at 227-51, 260-300 (Cordis expert testimony regarding the Palmaz-Schatz stent); 343-60, 363-67, 424-33 (J. Palmaz testimony regarding the Palmaz-Schatz stent and the '332 patent).
Trial Transcript from Nov. 28, 2000 at 649-71.
Trial Transcript from Nov. 29, 2000 at 791-816, 859-870, 953-62 (Cordis expert testimony regarding the '332 patent and the Palmaz-Schatz stent).

Trial Transcript from Nov. 30, 2000 at 1018 (Cordis expert testimony regarding the '332 patent); 1062-80, 1108-1111 (R. Croce testimony regarding the Palmaz-Schatz stent); 1169-70, 1205-17, 1236-45 (Cordis expert testimony regarding the '332 patent).
Trial Transcript from Dec. 1, 2000 at 1352-54 (Cordis expert testimony regarding the '332 patent); 1364-1442 (R. Schatz testimony); 1493-1508, 1552-69 (BSC expert testimony regarding the '332 patent and the Palmaz-Schatz stent).
Trial Transcript from Dec. 4, 2000 at 1602-12, 1638-51, 1713-14, 1730-61, 1811-14, 1823-36 (BSC expert testimony regarding the alleged obviousness of the '332 patent, the prior art and the Palmaz-Schatz stent).
Trial Transcript from Dec. 6, 2000 at 2318-27, 2342-58 (BSC expert testimony regarding the '332 patent).
Trial Transcript from Dec. 7, 2000 at 2549-52 (Cordis expert testimony regarding the '332 patent); 2575-2579, 2591-92, 2630-31, 2649, 2669-71, 2684-85, 2688, 2708-10, 2725-27 (Attorney closing argument regarding '332 patent); 2742-46 Q'ury instructions as to the meaning of the limitations fo the claims of the '332 patent).
Trial Transcript from Dec. 11, 2000 at 2817-22 (reading of jury verdict).
Jury verdict, dated Dec. 11, 2000.
D.I. 699, Motion by Defendant BSC and Scimed Life Systems, Inc. For Summary Judgment of Invalidity of U.S. Patent No. 5,902,332 dated Apr. 4, 2000.
D.I.896, Order Denying Motion for Summary Judgment of Invalidity and Unenforceability of Claims 1, 3, and 5 of the U.S. Patent No. 5,902,332 Denying {699-1} Motion for Summary Judgment of Invalidity of U.S. Patent No. 5,902,332 dated Oct. 12, 2000.
Wright et al., Percutaneous Endovascular Stent: An Experimental Study (Abstract), RSNA Meeting (Nov. 28, 1984).
Hearing Transcript from Feb. 10, 1998 at 122-32, 146-80 (Attorneys' opening remarks regarding '417 patent); 180-312 (R. Schatz testimony) [Portions of This Transcript Have Been Removed As Confidential].
Hearing Transcript from Feb. 11, 1998 at 427-575, 577-651 (Cordis expert testimony regarding the '417 patent, the prior art and the Palmaz-Schatz stent).
Hearing Transcript from Feb. 13, 1998 at 1121-1261 (Guidant expert testimony regarding the alleged obviousness of the '417 patent, the prior art and the Palmaz-Schatz stent). [Portions of This Transcript Have Been Removed As Confidential].
Order by J. Robinson denying Cordis' Motion for a Preliminary Injunction Against ACS dated Jul. 17, 1998.
ACS, Inc.'s and Guidant Corp.'s Opening Brief in Support of Their Motion for Summary Judgment of Invalidity of U.S. Patent No. 5,102,417 dated Aug. 27, 1998.
Plaintiffs' Answering Brief in Opposition to ACS' and BSC' Motion for Summary Judgment on Obviousness dated Sep. 24, 1998.
Order dated Mar. 31, 2000.
Schatz Deposition Testimony; May 15, 1996: 79-83, 89-92, 105-107 and 153-161.
Schatz Deposition Testimony; May 16, 1996: 555-564, 569-572.
Schatz Deposition Testimony; Jan. 18, 1998: 67-73, 108-110.
Schatz Deposition Testimony; Jul. 14, 1998: 69-77, 108-112, 119-123.
Schatz Deposition Testimony; Jul. 12, 1999: 88-91, 132-135, 144-149, 218-223, 231-242.
Schatz Deposition Testimony; Jul. 13, 1999: 251-334, 339-345, 374-416.
Schatz Deposition Testimony; Jul. 14, 1999: 454-550.
Schatz Deposition Testimony; Jul. 15, 1999: 560-614.
Schatz Deposition Testimony; Dec. 2, 1999: 906-911, 928-942, 945-963, 976-978, 1029-1034, 1038-1042.
Palmaz Deposition Testimony, Nov. 5, 1991: 160-172.
Palmaz Deposition Testimony, Feb. 5, 1995: 710-727.
Palmaz Deposition Testimony, Jul. 16, 1998: 55-56; 81-82.
Palmaz Deposition Testimony, Jul. 28, 1999: 560-568, 570-579.
Palmaz Deposition Testimony, Jul. 29, 1999: 778-785.
Palmaz Deposition Testimony, Aug. 31, 1999: 1403-1452.
Palmaz Deposition Testimony, Sep. 2, 1999: 1953-1960.

Palmaz Deposition Testimony, Oct. 14, 1999: 2201-2209; 2275-2342; 2371-2411.
Palmaz Deposition Testimony, Oct. 15, 1999: 2424-2497; 2508-2589.
Palmaz Deposition Testimony, Oct. 16, 1999: 2853-2860.
Tobor Deposition Testimony, Jun. 17, 1999: 837-958.
Tobor Deposition Testimony, Jun. 18, 1999: 1095-1184.
Tobor Deposition Testimony, Dec. 1, 1999: 1217-1371.
Tobor Deposition Testimony, Dec. 2, 1999: 1398-1414; 1444-1508; 1532-1548.
Tobor Deposition Testimony, Dec. 3, 1999: 1652-1653; 1662-1672; 1683-1694.
Kula Deposition Testimony, Apr. 20, 1999: 268-169.
Kula Deposition Testimony, Nov. 16, 1999: 660-675; 680-694; 748-755; 774-821.
Kula Deposition Testimony, Nov. 18, 1999; 176-223.
Expert Report of Dr. Rodney S. Badger on Behalf of Medtronic AVE, Inc. (Jan. 31, 2000).
Expert Report of Dr. Joseph Bonn on Behalf of Medtronic AVE, Inc. (Jan. 31, 2000).
Deposition of Dr. Joseph Bonn dated Mar. 14, 2000.
Rebuttal Expert Report of Nigel Buller, B.Sc., M.D., F.R.C.P. (Mar. 2000).
Second Supplemental Rebuttal Expert Report of Nigel Buller, B.Sc., M.B., F.R.C.P. (Aug. 17, 2004).
Rebuttal Expert Report of John M. Collins, PH.D. (Feb. 2000).
Expert Report of David C. Cumberland, M.D. (Jan. 24, 2000).
Expert Report of John T. Goolkasian (Feb. 2000).
Deposition of Richard R. Heuser, M.D. (Sep. 7, 2004).
Deposition of Henry R. Piehler (Sep. 10, 2004).
Deposition of Ronald J. Solar (Mar. 22, 2000).
Deposition of Ronald J. Solar (Mar. 23, 2000).
Deposition of Ronald J. Solar (Apr. 12, 2000).
Expert Report of Dr. Arina Van Breda on Behalf of Medtronic AVE, Inc. (Jan. 31, 2000).
Deposition of Arina Van Breda (Mar. 24, 2000).
Deposition of Arina Van Breda (Aug. 21, 2004).
Expert Report of John F. Witherspoon (Jan. 24, 2000).
Supplemental Expert Report of John F. Witherspoon (Oct. 27, 2000).
Deposition of John F. Witherspoon (Mar. 8, 2000).
Palmaz et al., Article: Normal and Stenotic Renal Arteries: Experimental Balloon Expandable Intraluminal Stenting, Radiology, Sep. 1987. (AVE 84).
Julio C. Palmaz, Article: "Expandable vascular endoprosthesis." (AVE 132).
Duprat et. al., Article: Flexible Balloon-Expandable Stent for Small Vessels Duprat et. al. Radiology, vol. 162, pp. 276-278, 1987. (AVE 134).
Coons et. al., Article: "Large-Bore, Long Biliary Endoprosthesis (Biliary Stents) for Improved Drainage," Radiology, vol. 148, pp. 89-94, 1983. (AVE 143).
Honickman et al., Article: "Malpositioned Biliary Endoprosthesis, Technical Developments And Instrumentation," vol. 144, No. 2., 1982. (AVE 144).
Harries-Jones, et al., Article: "Repositioning of Biliary Endoprosthesis with Gruntzig Balloon Catheters," AJR, vol. 138, pp. 771-772, 1982. (AVE 153).
Charnsangavej et al., Article "Stenosis of the Vena Cava: Preliminary Assessment of Treatment with Expandable Metallic Stents," Radiology, vol. 161, pp. 295-298, 1986. (AVE 359).
Article "Tracheobronchial Tree: Expandable Metallic Stents Used in Experimental and Clinical Applications," Radiology, vol. 158, pp. 309-312, 1986. (AVE 364).
T. Yoshioka, et al., AIR Article: "Self-Expanding Endovascular Graft: An Experimental Study in Dogs", vol. 151, pp. 673-676, 1988. (AVE 438).
Article: "Expandable Intraluminal Vascular Graft: A Feasibility Study," Surgery, vol. 99, pp. 199-205, 1986. (AVE 461).
Lawrence et al., Article: "Percutaneous Endovescular Graft: Experimental Evaluation." Radiology, vol. 163, pp. 357-360, 1987. (AVE 671).

Palmaz et al., Article: Expandable Intraluminal Graft: A Preliminary Study, Nov. 17-22, 1985, Radiology, vol. 156, pp. 73-77, 1985. (AVE 1224).
Fallone et al., "Elastic Characteristics of the Self-Expanding Metallic Stents," Investigative Radiology, vol. 23, pp. 370-376, 1988. (AVE 1953).
Palmaz Paper Entitled "Research Project Expandable Vascular Endoprosthesis" May 18, 1983.
Rousseau, et al., Publication: "Percutaneous Vascular Stent: Experimental Studies & Preliminary Clinical Results in Peripheral Arterial Diseases," in Inter. Angio, vol. 6, 153-161, 1987. (AVE 3301).
Rousseau, et al., Publication: "Self-Expanding Endovascular Prostesis: An Experimental Study," Radiology, vol. 164, pp. 709-714, 1987. (AVE 3303).
Wallace, et al., Article: "Tracheobronchial Tree: Expandable Metallic Stents Used in Experimental and Clinical Applications," Radiology, vol. 58, pp. 309-312, 1986. (DBX 2938).
Palmaz et al., Article: "Expandable Intraluminal Graft: A Preliminary Study," Radiology, vol. 156, pp. 73-77 (DBX 4595).
Program for the 12th Annual Course on Diagnostic Angiography and Interventional Radiology Mar. 23-26, 1987 sponsored by The Society of Cardiovascular and Interventional Radiology (DBX 6235).
Preliminary Motion for Judgment re: Wolff claims 1, 2-8, 10, 15 and 19 (DBX6759).
Palmaz Declaration (DBX 7069).
Letter from Gaterud to Dr. Palmaz dated Jul. 5, 1988 with attached document entitled: "Segmented, balloon-expandable stents." (DBX 7160).
Duprat et al., Article: "Flexible Balloon-Expandable Stent For Small Vessels," Radiology, vol. 168, pp. 276-278, 1987 (PX 82).
Drawing Sent to Bodic on Mar. 17, 1986 (PX 374).
Letter from Dr. Palmaz to R. Bowman enclosing a model of the flexible coronary graft dated Mar. 17, 1986 (PX 337).
Lab Notebook pages dated Jul. 30, 1987 from Rodney Wolff (COR 185596-597) (PX621A).
Charnsangavej, et al., Article: "Stenosis of The Vena Cava Prelimimnary Assessment of Treatment with expandable Metallic Stents," Radiology, vol. 161, No. 2, pp. 295-298 with attached photographs, 1986. (API 72).
J. Palmaz: The Current Status of Vascular Prostheses, published by SCIR in the Twelfth Annual Course on Diagnostic Angiography And Interventional Radiology Mar. 23-26, 1987. (API 73).
Amendment in Response to Office Action of Oct. 18, 1988 in re: Application of Julio Palmaz S/N 174,246. (API 152).
Article: Wallace, et al., Tracheobronchial Tree: Expandable Metallic Stents Used in Experimental and Clinical Applications Work In Progress, Radiology, vol. 158, pp. 309-312. (API 295).
Reply of Senior Party Schatz To Patentee Wolffs Opposition To The Belated Motion For Judgment Of Applicant Schatz With Regard To Wolff Claims 1, 2-8, 10, 11, 13-17, And 19 (COR 186450-455) (API 310).
Brief Of Senior Party Schatz At Final Hearing (API 313).
Letter from Ron Sickles to Ben Tobor dated Feb. 10, 1988 (Exhibit 42).
Letter from R.O. Sickles to Mike Tatlow dated May 12, 1988 (Exhibit 43).
Letter from R. 0. Sickles to Richard Schatz dated Jun. 2, 1988 (Exhibit 44).
Letter from Richard Schatz to Raimund Erbel dated Jun. 3, 1988 (Exhibit 45).
Letter from Richard Schatz to Mike Schuler dated Aug. 29, 1991 (Exhibit 48).
Minutes of J&J Stent Project Review Meeting dated Jan. 21, 1988 (Exhibit 7).
Preliminary Motion for Judgment with Regard to Wolff Claims 1, 2-8, 10, 11, 13-17, and 19. (Exhibit 67).
Declaration of Richard A Schatz. (Exhibit 75).
Belated Motion for Judgement with Regard to Wolff Claims 1, 2-8, 10, 11, 13-17 and 19. (Schatz—Exhibit 77).
Letter from Dr. Schatz to Mr. Tobor, dated Jun. 3, 1988. (Exhibit 122).

Letter from Dr. Schatz to Mr. Romano, dated Nov. 28, 1988. (Exhibit 131).
Letter from Mr. Sickles to Mr. Tobor, dated Feb. 10, 1988 (Exhibit 145).
Richard A. Schatz, Article titled: "A View of Vascular Stents" Circulation, vol. 79, No. 2, pp. 445-457, 1989. (Exhibit 194).
Senior Party Schatz's reply to Patente Wolffs Opposition to the Preliminary Motion Of Applicant Schatz for Judgment with regard to Wolff Claims 1, 2-8, 10, 11, and 13-17. (Exhibit 69).
Wallace, et al., Article: "Tracheobronchial Tree: Expandable Metallic Stents Used in Experimental and Clinical Applications' Work In Progress," Radiology, vol. 158, pp. 309-312, 1986. (Exhibit 165).
Charnsangavej, et al., Article: "Stenosis of The Vena Cava Prelimimnary Assessment of Treatment with expandable Metallic Stents," Radioloby, vol. 161, No. 2, pp. 295-298 with attached photographs, 1986. (Exhibit 167).
David D. Lawrence et al., Publication: Percutaneous Endoyascular Graft: Experimental Evaluation[1], Radiology, pp. 357-360, 1987. (Exhibit 173).
Charles E. Putnam, M.D., Cover and article from "Investigative Radiology",vol. 23. No. 5, May 1988. (Exhibit 177).
Robert N. Berk, Cover and article from "American Journal of Roentology", pp. 673-676, 1988. (Exhibit 178).
Declaration of John S. Kula Under 37 CFR § 1.672. (Kula—Exhibit 77).
Yoshioka et al., Article: "Self-Expanding Endovascular Graft: An Experimental Study in Dogs" AJR, vol. 151, pp. 673-676, 1988. (PX 100).
Palmaz, et al., Article: Expandable Intraluminal Graft: A Preliminary Study Work in Progress[1], Radiology, vol. 156, No. 1, pp. 73-77, 1985. (PX 101).
Declaration of Richard Schatz Under 37 C.F.R.§ 1.672. (PX 106).
Charnsangavej et al., Article: "Stenosis of the Vena Cave: Preliminary Assessment of Treatment with Expandable Metallic Stents," Radiology, vol. 161, pp. 295-298, 1986. (PX 143).
Wallace, et al., Article: Tracheobronchial Tree: Expandable Metallic Stents Used in Experimental and Clinical Applications Work in Progress[1], Radiology, vol. 158, pp. 309-312,1986. (PX 144).
Gina Kolata, News Article: NY Times, "Devices That Opens Clogged Arteries Gets a Falling Grade in a New Study", pp. 16-18, Jan. 3, 1991. (PX 186).
Duprat, et al., Article: "Flexible Balloon- Expanded Stent for Small Vessels Work in Progress[1]", Radiology, vol. 162, pp. 276-278, 1987. (PX 207).
Letter from Palmaz to Bowman dated Mar. 17, 1986. (PX 350).
Memo re: Minutes of Stent Project Review- San Antonia- Mar. 15, 1988. (PX 651).
Kuntz, et al., Article: Clinical Cardiology Frontiers: "Defining Coronary Restenosis, Newer Clinical and Angiographic Paradigms", Circulation, Sep. 1993, vol. 88, No. 3, pp. 1310-1323. (PX 854).
Belated Motion for Judgment with regard to Wolff Claimsl, 2-8, 10, 11, 13-17, and 19. (PX 1410).
Drawing of Sprial Stent (sent to Bodic Mar. 17, 1986). (PX2933).
Wright et al., Article: "Percutaneous Endovascular Stents: An Experimental Evaluation," Radiology, vol. 156, pp. 69-72, 1985. (PX 3093).
Charnsangavej et al., Article: "A New Expandable Metallic Stent for Dilation of Stenotic Tubular Structures: Experimental and Clinical Evaluation," Houston Medical Journal, vol. 3, pp. 41-51, Jun. 1987. (PX 3207).
In re Application of Wiktor, Appln. No. 69,636, Response to Office Action dated Mar. 17, 1988. (PX3236).
Transmittal Letter of Response to First Office Action in '417 patent. (PX 3993).
Letter from B. Tobor to R. Schatz dated Jul. 23, 1991. (PX 3996).
Mullins et al., Article: "Implantation of balloon-expandable intravascular grafts by catherization in pulmonary arteries and systemic veins," Circulation, vol. 77, No. 1, pp. 188-189,1988. (PX4049).
Schatz et al., Article: "Intravascular Stents for Angioplasty," Cardio, 1997. (PX 4050).
Schatz et al., Article: "New Technology in Angioplasty Balloon-Expandable Intravascular Stents, New Developments in Medicine," vol. 2, No. 2 pp. 59-75, 1987. (PX405I).
Richard A. Schatz, Article: "Introduction to Intravascular Stents," Cardiology Clinics, vol. 6, No. 3, pp. 357-372, 1988. (PX 4052).
Richard A. Schatz, Article: "A View of Vascular Stents," Circulation, vol. 79, No. 2, pp. 445-457, 1989. (PX4053).
Wang et al., Article: "An Update on Coronary Stents," Cardio, pp. 177-186, 1992. (PX 4054).
Richard A. Schatz, Article: "New Technology in Angioplasty: Balloon-Expandable Starts," Medicamundi, vol. 33, No. 3, pp. 112-116, 1988. (PX 4055).
Letter from Tobor to Schatz dated Sep. 29, 1988. (PX 1395).
Verified Statement of Facts by Unnamed Inventor R.A. Schatz document filed in U.S. Patent and Trademark Office on Sep. 8, 1989. (PX 3677).
Declaration of John S. Kula Under 37 CFR § 1.672 (Exhibit 329).
Letter to Mike Schular from R.A. Schatz dated Aug. 29, 1991. (Exhibit 402).
Articulated, Balloon—Expandable Stents, (DBX 7159).
J. Rosch et al., Experimental Intrahepatic Portacaval Anastomosis: Use of Expandable Gianturco Stents, Radiology, vol. 162, pp. 481-485, 1987.
J. Rosch et al., Modified Gianturco Expandable Wire Stents In Experimental and Clinical Use, Ann Radiol, vol. 31, No. 2, pp. 100-103, 1987.
J. Rosch et al., Gianturco Expandable Stents In the Treatment of Superior Vena Cava Syndrome Recurring After Vena Cava Syndrome Recurring After Maximum-Tolerance Radiation, Cancer, vol. 60, pp. 1243-1246, 1987.
I.E. Gordon, Structures or Why Things Don't Fall Down, Penguin Books, pp. 45-59, 132-148, 210-244, 377-383.
Maass et al., Radiological Follow-up of Transluminally Inserted Vascular Endoprostheses: An Experimental Study Using Expanding Spirals, Radiology, vol. 152, pp. 659-663, 1984.
Argument submitted re EP 861 15473 dated Jan. 20, 1995. (AVE 2478).
Verified Statement of Facts by Julio C. Palmaz dated Aug. 4, 1989. (PX 3662).
Papanicolaou et al., Insertion of a Biliary Endoprosthesis Using A Balloon Dilatation Catheter, Gastrointest Radiology, vol. 10, pp. 394-396, 1985.
Palmaz et al., Atheroscierotic Rabbit Aortas: Expandable Intraluminal Grafting, Radiology, vol. 168, pp. 723-726, 1986.
Palmaz, The Current Status of Vascular Prostheses; Rosch et al., Gianturco, Expandable Stents in Experimental and Clinical Use, SCIVR, pp. 118-124, 1987.
Rosch et al., Abstract: Modified Gianturco Expandable Wire Stents in Experimental and Clinical Use, CIRSE, Porto Cervo, Sardinia, May 25-29, 1987.
Rosch et al., Gianturco Expandable Wire Stents in the Treatment of Superior Vena Cava Syndrome Recurring After Maximum-Tolerance Radiation, Cancer, vol. 60, pp. 1243-1246, 1987.
Mirich et al., Percutaneously Placed Endovascular Grafts for Aortic Aneurysms: Feasibility Study, Radiology, vol. 170, pp. 1033-1037, 1989.
Dotter, Transluminally-placed Coilspring Endarterial Tube Grafts, Investigative Radiology, vol. 4, Sept.-Oct., pp. 329-332, 1969.
Palmaz et al., Abstract: Expandable Intraluminal Graft: A Preliminary Study, Radiology, vol. 153 (P), Nov. 1983: 70th Scientific Assembly and Annual Meeting.
Cragg et al, Nonsurgical Placement of Arterial Endoprostheses: A New Technique Using Nitinol Wire, Radiology, vol. 147, pp. 261-263, Apr. 1983.
J. Rosch et al., Gianturco Expandable Stents in Experimental and Clinical Use, Program: "Twelfth Annual Course on Dignostic Angiography and Interventional Radiology" (Society of Cardiovascular and Interventional Radiology, Pittsburgh, PA), Mar. 23-26, 1987 (the second Monofilament Article).
Uchida et al., Modifications of Gianturco Expandable Wire Stents, AIR, vol. 150, pp. 1185-1187,1988.
Palmaz, Balloon-Expandable Intravascular Stent, AJR, vol. 1510, pp. 1263-1269.

*Cordis Corporation v. Advanced Cardiovascular Systems, Inc., Guidant Corporation, Arterial Vascular Engineering, Inc., Boston Scientific Corporation and SCMED Life System, Inc.*, Plaintiffs Complaint, Oct. 23, 1997 (Case No. 97-550-SLR).

*Arterial Vascular Engineering, Inc. v. Cordis Corporation, Johnson & Johnson and Expandable-Grafts Partnership*, Plaintiffs First Amended Complaint for Declaratory Relief of Patent Validity, Unenforceability, Noninfiingement, and for Antitrust Violations, Jan. 27, 1998 (Civil Action No. 97-700).

*Arterial Vascular Engineering, Inc. v. Cordis Corporation, Johnson & Johnson and Expandable-Grafts Partnership, Cordis Corporation and Johnson & Johnson's Answer and Counterclaim*, Feb. 27, 1998 (Civil Action No. 97-700-SLR).

*Arterial Vascular Engineering, Inc. v. Cordis Corporation, Johnson & Johnson and Expandable-Grafts Partnership, Expandable-Graft Partnership's Answer*, Feb. 27, 1998 (Civil Action No. 97-700-SLR).

*Arterial Vascular Engineering, Inc. v. Cordis Corporation, Johnson & Johnson and Expandable-Grafts Partnership*, Reply of Plaintiff Arterial Vascular Engineering, Inc. To Counterclaims of Defendant Cordis Corporation, Mar. 31, 1998 (Civil Action No. 97-700-SLR).

*Arterial Vascular Engineering, Inc. v. Cordis Corporation, Johnson & Johnson and Expandable-Grafts Partnership*, Reply of Plaintiff Arterial Vascular Engineering, Inc. To Counterclaims of Defendant Expandable Grafts Partnership, Mar. 31, 1998 (Civil Action No. 97-700-SLR).

*Cordis Corporation v. Advanced Cardiovascular Systems, Inc. and Guidant Corporation* Cordis Corporation's Motion for a Preliminary Injunction, Oct. 8, 1997 (Civil Action No. 97-550).

*Cordis Corporation v. Advanced Cardiovascular Systems, Inc., Guidant Corporation Arterial Vascular Engineering, Inc., Boston Scientific Corporation and SCJJVIED, Inc., Cordis 's Motion for Preliminary Injunction Against Arterial Vascular Engineering, Inc.*, Dec. 29, 1997 (Case No. 97-550-SLR).

Deposition of R. Schatz, M.D. in *Cordis Corporation v. Advanced Cardiovascular Systems, Inc.*, taken on Jan. 8, 1998 (Civil Action No. 97-550 SLR).

Deposition of Lee P. Bendel in *Cordis Corporation v. Advanced Cardiovascular Systems, Inc.*, taken on Jan. 22, 1998 (Civil Action No. 97-550 SLR).

Deposition of Julio Cesar Palmaz in *Cordis Corporation v. Advanced Cardiovascular Systems, Inc.*, taken on Dec. 29, 1997 (Civil Action No. 97-550 SLR).

Deposition of Richard A. Bowman in *Cordis Corporation v. Advanced Cardiovascular Systems, Inc.*, taken on Jan. 9, 1998 (Civil Action No. 97-550 SLR).

Deposition of Gary Schneiderman in *Cordis Corporation v. Advanced Cardiovascular Systems, Inc.*, taken on Jan. 16, 1998 (Civil Action No. 97-550 SLR).

Deposition of David Pearle, M.D. in *Cordis Corporation v. Advanced Cardiovascular Systems, Inc.*, taken on Jul. 10, 1998 (Civil Action No. 97-550 SLR).

Preliminary Injuction hearing testimony taken on Feb. 9-13, 1998 (Civil Action No. 97-550 SLR).

*Cordis Corporation v. Advanced Cardiovascular Systems, Inc.*, et al., (Civil Action No. 97-550 SLR) and *Cordis Corporation v. Advanced Cardiovascular Systems, Inc.* Et al. (Civil Action No. 98-65-SLR), Opening Post Hearing Brief of Plaintiff Cordis Corporation in Support of Motion for Preliminary Injunction, Mar. 6, 1998 (Portions relevant to patent claim construction and patent validity issues).

*Cordis Corporation and Expandable Grafts Partnership v. Advanced Cardiovascular Systems, Inc.* et al., Post-Hearing Reply Brief of Plaintiff Cordis Corporation in Support of Its Motion for Preliminary Injunction, Apr. 10, 1998 (Case No. 97-550 SLR) (Portions relevant to patent validity issues).

*Cordis Corporation and Expandable Grafts Partnership v. Advanced Cardiovascular Systems, Inc.*, et al., Plaintiffs Motion for a Preliminary Injunction Against Boston Scientific Corporation and SCLMED Life Systems, Inc. And Memorandum is Support, Apr. 13, 1998 (Case No. 97-550-SLR).

*Cordis Corporation and Expandable Grafts Partnership v. Advanced Cardiovascular Systems, Inc.*, et al., Judge Robinson's Order Denying Plaintiffs Motion for a Preliminary Injunction, Jul. 17, 1998 (Civil Action No. 97-550 SLR).

*Cordis Corporation and Expandable Grafts Partnership v. Advanced Cardiovascular Systems, Inc.*, et al., Defendant Boston Scientific Corporation and SCTMED Life Systems, Inc.'s Motion for Summary Judgment of Invalidity of U.S. Patent No. 5,102,417, Aug. 27, 1998 (Civil Action No. 97-550-SLR).

*Boston Scientific Limited*, et al. v. *Expandable Grafts Partnership*, Plaintiff's Statement of Claim, Mar. 13, 1997 (UK Action No. 1493).

*Boston Scientific Limited*, et al. v. *Expandable Grafts Partnership*, Defendant's Amended Defense and Counterclaim, Aug. 14, 1997 (UK Action No. 1493).

*Boston Scientific Limited*, et al. v. *Expandable Grafts Partnership*, Petition for Revocation, Mar. 13, 1997 (UK Action No. 1497).

*Boston Scientific Limited*, et al. v. *Expandable Grafts Partnership*, Particulars of Objections, Mar. 13, 1997 (UK Action No. 1497).

*Boston Scientific Limited*, et al. v. *Expandable Grafts Partnership and Boston Scientific Limted* et al., v. *Julio C. Palmaz, Boston's Skeleton Argument* (UK Action Nos. 1493, 1495, 1496, and 1497).

*Boston Scientific Limited*, et al. v. *Julio C. Palmaz and Expandable Grafts Partnership*, Skeleton Argument of Palmaz/EGP, Mar. 19, 1998 (UK Action Nos. 1493, 1495, 1496 and 1497).

*Boston Scientific Limited*, et al. v. *Julio C. Palmaz and Expandable Grafts Partnership*, EGP's Final Submissions, Apr. 2, 1998 (UK Action Nos. 1493, 1495, 1496 and 1497).

*Boston Scientific Limited*, et al. v. *Julio C. Palmaz and Expandable Grafts Partnership*, Judgment, Jun. 26, 1998 (UK Action Nos. 1493, 1495, 1496 and 1497).

Rosch, Modified Gianturco Expandable Wire Stents in Experimental and Clinical Use, CJJR.SE 1987 Presentation: see Witness Statement of Josef Rosch from U.K. Proceeding.

Statement of Claim by Boston Scientific et al. against Expandable Grafts Partnership et al., in *EPG* et al., v. *Boston Scientific* et al. in Netherlands (Mar. 13, 1997).

Motion for Joinder of Actions, Change of Claim and Statement of Claim filed by Expandable Grafts Partnership et al. in *EPG* et al. v. *Boston Scientific* et al. In Netherlands (Apr. 22, 1997).

Opinion of K.J. Merman filed in *EPG* et al. v. *Boston Scientific* et al. in Netherlands (Aug. 29, 1997).

Expert report of Dr. Nigel Buller in *EPG* et al. v. *Boston Scientific* et al. in Netherlands (Aug. 28, 1997).

Expert report of Lee P. Bendel in *EPG* et al. v. *Boston Scientific* et al. in Netherlands (Aug. 28, 1997).

Memorandum or Oral Pleading in *EPG* et al. v. *Boston Scientific* et al. in Netherland (Sep. 12, 1997).

Plea Notes of P. A.M. in *EPG* et al. v. *Boston Scientific* et al. in Netherlands (Mar. 10, 1998).

Decision of Court of Appeals in *EPG* et al. v. *Boston Scientific* et al. In Netherlands (Apr. 23, 1998).

Translation of Nullity Action Against EPO 0 364 787 by Biotronik in Germany.

Translation of Nullity Action Against EPO 0 335 341 by Biotronik in Germany.

Translation of EPG Response to Nullity Action Against EP 0 364 787 by Biotronik in Germany.

Translation of EPG Response to Nullity Action EP 0 335 341 by Biotronik in Germany.

Nullity Suit Against EP-B1-0 335 341 Brought by Boston Scientific in Germany.

Translation of Opposition filed by Terumo Corp. Against Japan Patent No. 2680901.

Translation of Decision on Opposition Against Japan Patent No. 2680901.

Memorandum Order of the Court dated Sep. 7, 2000, concerning disputed claim construction.

Translation of Judgment in Nullity Action Against EP 0 364 787 by Biotronik in Germany.

Translation of Judgment in Nullity Action Against EP 0 335 341 by Biotronik in Germany.

Trial transcript from Mar. 17, 2005 at 171-172, 191-192.

Trial transcript from Mar. 18, 2005 at 282-285, 325-327, 349-351.

Trial transcript from Mar. 21, 2005 at 721-726.

Trial transcript from Mar. 24, 2005 at 1387.
Trial transcript from Jul. 26, 2005.
BSC's Opening Brief in Support of Its Motion for Judgment as a Matter of Low or, in the Alternative, for a New Trial, dated Mar. 16, 2001.
Cordis' Answering Brief in Opposition to BSC's Motion for JMOL or a New Trial on the Palmaz '762 Patent and the Schatz '332 Patents, dated Apr. 17, 2001.
BSC'Reply Brief in Support of Its Motion for Judgment as a Matter of Law or, in the Alternative, for a New Trial, dated May 11, 2001.
J. Rosch et al., Abstract, Expandable Gianturco-Type Wire Stents in Experimental Intrahepatic Portacaval Shunts, Program: "72nd Scientific Assembly and Annual Meeting of the Radiological Society of North America", Nov. 30-Dec. 5, 1986, Radiology, vol. 161, pp. 40-41, 1986.
*Cordis Corporation* v. *Boston Scientific*, Order Dated Mar. 27, 2006 (97-550-SLR).
*Cordis Corporation* v. *Boston Scientific*, Judgment in a Civil Case Dated Mar. 27, 2006 (97-550-SLR).
*Cordis Corporation* v. *Boston Scientific*, Memorandum Opinion Dated Mar. 27, 2006 (97-550-SLR).
*Cordis Corporation and Expandable Grafts Partnership* v. *Advanced Cardiovascular Systems, Inc., Guidant Corporation, Arterial Vascular Engineering, Inc., Boston Scientific Corporation and SCIMED Life Systems, Inc.*, Answer and Counterclaims of Defendant Advanced Cardiovascular Systems, Inc., Apr. 8, 1998 (Case No. 97-550-SLR).
*Boston Scientific Limited* et al. v. *Expandable Grafts Partnership and Boston Scientific Limited* et al. v. *Julio C. Palmaz*, Boston's Closing Submissions (UK Action Nos. 1493, 1495, 1496 and 1497).
*Cordis Corporation* v. *Advanced Cardiovascular Systems, Inc., Guidant Corporation, Arterial Vascular Engineering, Inc., Boston Scientific Corporation and SCIMED Life Systems, Inc.*, Defendants' Answer, Nov. 12, 1997 (Case No. 97-550-SLR).
Statement of Rejoinder in the Action on the Merits, Also Including an Amendment of Defendant's Final Position in the Principal Action, as Well as the Provisional Statement of Rejoinder in the Action on the Counterclaim in *EPG* et al. v. *Boston Scientific* et al. In Netherlands (Feb. 10, 1998).
Statement of Answer in the Ancillary Appeal in *EPG* et al. v. *Boston Scientific* et al. in Netherlands (Mar. 10, 1998).
Appeal filed by Expandable Grafts Partnership et al. in *EPG* et al. v. *Boston Scientific* et al. in Netherlands (Nov. 12, 1997).
Title filed by Boston Scientific et al. in *EPG* et al. v. *Boston Scientific* et al. in Netherlands (Jan. 22, 1998).
Deposition of Richard Schatz, M.D. in *Cordis Corporation* v. *Advanced Cardiovascular Systems, Inc.* taken on Jul. 14, 1998 (Civil Action No. 97-550-SLR).
Jury Verdict form from the *Cordis Corporation* et al v. *Boston Scientific Corporation*, et al liability trial, undated.
Trial testimony transcripts from the *Cordis Corporation* et al. v. *Boston Scientific Corporation* et al. liability trial dated Nov. 27-Dec. 1, Dec. 4-8 and Dec. 11, 2000.
*Boston Scientific SCIMED, Inc. and Boston Scientific Corporation* v. *Cordis Corporation and Johnson and Johnson, Inc.*, Opening Expert Report of Stephen R. Hanson, Ph.D. (Civil Action No. 03-283-SLR).
*Boston Scientific SCIMED, Inc. and Boston Scientific Corporation* v. *Cordis Corporation and Johnson and Johnson, Inc.*, Opening Expert Report of Robson F. Storey, Ph.D. (Civil Action No. 03-283-SLR).
*Boston Scientific SCIMED, Inc. and Boston Scientific Corporation* v. *Cordis Corporation and Johnson and Johnson, Inc.*, Rebuttal Expert Report of Kinam Park, Ph.D. (Civil Action No. 03-283-SLR).
*Cordis Corporation* v. *Boston Scientific Corporation and SCIMED Life Systems, Inc.* (C.A. No. 03-027-SLR) and *Boston Scientific SCIMED, Inc., and Boston Scientific Corporation* v. *Cordis Corporation and Johnson and Johnson, Inc.* (C.A. No. 03-283-SLR) Combined Post-Hearing Brief In Support Of Cordis Corporation's Motion For Preliminary Injunction in C.A. No. 03-027-SLR, And In Opposition to Plaintiffs' Motion For Preliminary Injunction in C.A. No. 03-283-SLR.

*Cordis Corporation* v. *Boston Scientific Corporation and SCIMED Life Systems, Inc.* (C.A. No. 03-027-SLR) *Boston Scientific SCIMED, Inc., and Boston Scientific Corporation* v. *Cordis Corporation and Johnson and Johnson, Inc.* (C.A. No. 03-283-SLR), Boston Scientific's Opening Post-Hearing Brief.
*Cordis Corporation* v. *Boston Scientific Corporation and SCIMED Life Systems, Inc.* (C.A. No. 03-027-SLR) *Boston Scientific SCIMED, Inc., and Boston Scientific Corporation* v. *Cordis Corporation and Johnson and Johnson, Inc.* (C.A. No. 03-283-SLR), Combined Post-Hearing Answering Brief In Support Of Cordis Corporation's Motion For Preliminary Injunction In C.A. No. 03-027-SLR, And In Opposition To Plaintiffs Motion For Preliminary Injunction In C.A. No. 03-283-SLR.
Wu et al., Silicone-covered self-expanding metallic stents for the palliation of malignant esophageal obstruction and esophagorespiratory fistulas: experience in 32 patients and a review of the literature, *Gastrointestinal Endoscopy*, 1994, pp. 22-33, vol. 40, No. 1, Portland Oregon.
Binmoeller, et al., Silicone-Covered Expandable Metallic Stents in the Esophagus: An Experimental Study, Endoscopy, 1992, pp. 416-420, vol. 24, Georg Thieme Verlag Stuttgart New York.
*Boston Scientific SCIMED, Inc., and Boston Scientific Corporation* v. *Cordis Corporation and Johnson and Johnson, Inc.*, Answering Memorandum in Opposition to Plaintiffs Motion for a Preliminary Injunction and Appendix thereto (Civil Action No. 03-283-SLR).
*Boston Scientific SCIMED, Inc., and Boston Scientific Corporation* v. *Cordis Corporation and Johnson and Johnson, Inc.*, Plaintiff s Reply Brief in Support of Their Motion for Preliminary Injunction.
Rhine, Polymers for Sustained Macromolecule Release: Procedures to Fabricate Reproducible Delivery Systems and Control Release Kinetics, *Journal of Pharmaceutical Sciences*, 1980, pp. 265-270, vol. 69, No. 3.
Langer et al., Controlled Release of Macromolecules From Polymers, *Biomedical Polymers Polymeric Materials and Pharmaceuticals for Biomedical Use*, 1980, pp. 112-137, Academic Press, Inc., New York, NY.
Langer et al., Applications of Polymeric Delivery Systems for Macromolecules and Factors Controlling Release Kinetics.
Rhine et al., A Method to Achieve Zero-Order Release Kinetics From Polymer Matric Drug Delivery Systems, pp. 67-72.
Langer et al., Polymers for the Sustained Release of Macromolecules: Controlled and Magnetically Modulated Systems, *Better Therapy With Existing Drugs: New Uses and Delivery Systems*; 1981, pp. 179-216, Merck Sharp & Dohme International, Rahway, NJ.
Hsieh, et al., Zero-Order Controlled-Release Polymer Matrices for Micro-and-Macromolecules, *Journal of Pharmaceutical Sciences*, 1983 pp. 17-22, vol. 72, No. 1.
Brown et al., In Vivo and In Vitro Release of Macromolecules from Polymeric Drug Delivery Systems, *Journal of Pharmaceutical Sciences*, 1983, pp. 1181-1185, vol. 72, No. 10.
Langer, Implantable Controlled Release Systems, *Pharmac. Ther.*, 1983, pp. 35-51, vol. 21, printed in Great Britain.
Kost et al., Controlled Release of Bioactive Agents, *Trends in Biotechnology*, 1984, pp. 47-51, vol. 2, No. 2, Elsevier BV Amsterdam.
Bawa et al., An Explanation for the Controlled Release of Macromolecules from Polymers, *Journal of Controlled Release*, 1985, pp. 259-267, vol. 1 Elsevier Science BV Amsterdam.
Leong et al., Polymeric controlled drug delivery, 1987, pp. 199-233, vol. 1/3, Elsevier Science Publishers BV Amsterdam.
Langer, Polymeric Delivery Systems, *Targeting of Drugs 2 Optimization Strategies*, 1989, pp. 165-174, Plenum Press, New York and London.
Langer, Biomaterials in Controlled Drug Delivery; New Perspectives from Biotechnological Advances; *Pharmaceutical Technology*, 1989, pp. 18, 23-24, 26, 28, 30.
Langer, Controlled Release Systems, pp. 115-124.
Laurencin et al., Polymeric Controlled Release Systems: New Methods for Drug Delivery, *Clinics in Laboratory Medicine*, 1987, pp. 301-323, vol. 7, No. 2, WB Saunders Company, Philadelphia.
Langer, Biopolymers in Controlled Release Systems, *Polymeric Biomaterials*, pp. 161-169.

Tsong-Pin Hsu et al., Polymers for the Controlled Release of Macromolecules: Effect of Molecular Weight of Ethylene-vinyl Acetate Copolymer, *Journal of Biomedical Materials Research*, 1985, pp. 445-460, vol. 19.

Langer, Polymers and Drug Delivery Systems, *Long-Acting Contraceptive Delivery Systems*, 1983, pp. 23-32, Harper & Row, Philadelphia, PA.

Langer, New Drug Delivery Systems: What the Clinician Can Expect, *Drug Therapy*, 1983, pp. 217-231.

Langer, et al., Chemical and Physical Structure of Polymers as Carriers for Controlled Release of Bioactive Agents: A Review, *Rev. Macromol. Chem. Phys.*, 1983, pp. 61-126.

Langer, Polymeric Delivery Systems for Controlled Drug Release, *Chem. Eng. Commun.* 1980, pp. 1-48-vol. 6, Gordon and Breach Science Publishers, Inc. USA.

Langer, et al., Biocompatibility of Polymeric Delivery Systems for Macomolecules, *Journal of Biomedical Materials Research*, 1981, pp. 267-277, vol. 15.

Langer, Controlled Release: A New Approach to Drug Delivery, *Technology Review*, 1981, pp. 26-34.

Langer, et al Sustained Release of Macromolecules from Polymers, *Polymeric Delivery Systems*, PGS. 175-176, Gordon and Breach Science Publishers, New York.

Langer, Polymers for the Sustained Release of Proteins and other Macromolecules, *Nature*, 1976, pp. 797, 263, 799-800, vol. 263, No. 5580.

Baker, et al., Controlled Release: Mechanisms and Rates (1974).

Hanson, et al., In Vivo Evaluation of Artificial Surfaces with a Nonhum Primate Model of Arterial Thrombosis,/ *Lab Clin. Med.*, Feb. 1980, pp. 289-304.

Baker, Controlled Release of Biologically Active Agents (1987) pp. 1-275.

*Cordis Corporation v. Boston Scientific Corporation* (CA. No. 03-27-SLR) and *Boston Scientific Scimed, Inc., v. Cordis Corporation and Johnson & Johnson, Incorporated* (CA. No. 03-283-SLR) Hearing Transcripts for Jul. 21, 2003, Jul. 22, 2003, Jul. 23, 2003.

*Cordis Corporation v. Boston Scientific Corporational et al.* (CA. No. 03-027-SLR), and *Boston Scientific Scimed, Inc.* et al. v. *Cordis Corporation* et al. (CA. No. 03-283-SLR), Boston Scientific's Post-Hearing Reply Brief and Exhibits Thereto, Sep. 12, 2003.

*Cordis Corporation v. Boston Scientific Corporation et al.* (CA. No. 03-027-SLR), and *Boston Scientific Scimed, Inc.* et al. v. *Cordis Corporation* et al. (CA. 03-283-SLR), Memorandum Order, Nov. 21, 2003.

*Cordis Corporation v. Boston Scientific Corporation et al.* (CA. No. 03-027-SLR), and *Boston Scientific Scimed, Inc.* et al. v. *Cordis Corporation* et al (CA. No. 03-283-SLR), Deposition Transcript of Julio C. Palmaz.

*Arterial Vascular Engineering, Inc.* v. *Cordis Corporation, Johnson & Johnson and Expandable Grafts Partnership*, Cordis Corporation and Johnson & Johnson's Answer and Counterclaim, Feb. 27, 1998 (Civil Action No. 97-700-SLR).

Plea Notes in *EPG* et al. v. *Boston Scientific* et al. in Netherlands (Sep. 12, 1997).

Provisional Judgment *EPG* et al. v. *Boston Scientific* et al. in Netherlands (Oct. 29, 1997).

Trial testimony transcripts from the Cordis Corporation et al. v. Medtronic AVE Inc., et al. liability trial dated Nov. 6-9, 13-17 and 20-21, 2000.

Jury verdict form from the *Cordis Corporation* et al. v. *Medtronic AVE, Inc.* et al. liability trial.

Hearing testimony transcript from the consolidated *Cordis Corporation* et al. v. *Medtronic AVE, Inc.* et al. and *Boston Scientific Corporation* et al. inequitable conduct hearing dated Feb. 7-9 and 12, 2001.

*Cordis Corporation* v. *Medtronic Ave., Inc.* et al, OPINION, 97-550-SLR, dated Mar. 28, 2002.

*Cordis Corporation* v. *Advanced Cardiovascular Systems, Inc.* et al. (CA. No. 97-550-SLR), *Medtronic AVE, Inc.* v. *Cordis Corporation* et al. (CA. No. 97-700-SLR), *Boston Scientific Corporation* v. *Athicon, Inc.* etal. (CA. No. 98-19-SLR), Expert Report of John T. Goolkasian, Esq.

*Cordis Corporation* v. *Advanced Cardiovascular Systems, Inc*et al. (CA. No. 97-550-SLR), *Medtronic A VE, Inc.* v. *Cordis Corporation* et al (CA. No. 97-700-SLR), *Boston Scientific Corporation* v. *Athicon, Inc.* et al (CA. 98-19-SLR), Expert Report of John F. Witherspoon.

Ruef, Johannes MD, et al.; "Flavopiridol Inhibits Smooth Muscle Cell Proliferation In Vitro and Neointimal Formation In Vivo After Carotid Injury In The Rat"; From the Division of Cardiology and Sealy Center for Molecular Cardiology, University of Texas Medical Branch, Galveston; Accepted Apr. 9, 1999; Circulation Aug. 10, 1999; pp. 659-665.

European Search Report EP 05 25 2466 dated Jul. 26, 2005.

European Search Report EP 05 25 2631 dated Jul. 26, 2005.

European Search Report EP 05 25 2478 dated Jul. 26, 2005.

Schuler, W. et al., "SDZ RAD, A New Rapamycin Derivative: Pharmacological Properties In Vitro and In Vivo," *Transplantation*, Jul. 5, 1997, 64(1), 36-42.

\* cited by examiner

DRUG/DRUG DELIVERY SYSTEMS FOR THE PREVENTION AND TREATMENT OF VASCULAR DISEASE

CROSS REFERENCE TO RELATED APPLICATIONS

This application is a continuation-in-part of U.S. application Ser. No. 09/850,293, filed May 7, 2001, now abandoned, which in turn claims priority of U.S. Provisional Application No. 60/263,979, filed Jan. 25, 2001, U.S. Provisional Application No. 60/263,806, filed January 24, 2001, U.S. Provisional Application No. 60/262,614, filed Jan. 18, 2001, U.S. Provisional Application No. 60/262,461, filed Jan. 18, 2001, and is a continuation-in-part of U.S. Application No. 09,575,480, filed May 19, 2000, now pending, which in turn claims priority of U.S. Provisional Application No. 60/204,4 17, filed May 12, 2000.

BACKGROUND OF THE INVENTION

1. Field of the Invention

The present invention relates to drugs and drug delivery systems for the prevention and treatment of vascular disease, and more particularly to drugs and drug delivery systems for the prevention and treatment of neointimal hyperplasia.

2. Discussion of the Related Art

Many individuals suffer from circulatory disease caused by a progressive blockage of the blood vessels that perfuse the heart and other major organs with nutrients. More severe blockage of blood vessels in such individuals often leads to hypertension, ischemic injury, stroke, or myocardial infarction. Atherosclerotic lesions, which limit or obstruct coronary blood flow, are the major cause of ischemic heart disease. Percutaneous transluminal coronary angioplasty is a medical procedure whose purpose is to increase blood flow through an artery. Percutaneous transluminal coronary angioplasty is the predominant treatment for coronary vessel stenosis. The increasing use of this procedure is attributable to its relatively high success rate and its minimal invasiveness compared with coronary bypass surgery. A limitation associated with percutaneous transluminal coronary angioplasty is the abrupt closure of the vessel which may occur immediately after the procedure and restenosis which occurs gradually following the procedure. Additionally, restenosis is a chronic problem in patients who have undergone saphenous vein bypass grafting. The mechanism of acute occlusion appears to involve several factors and may result from vascular recoil with resultant closure of the artery and/or deposition of blood platelets and fibrin along the damaged length of the newly opened blood vessel.

Restenosis after percutaneous transluminal coronary angioplasty is a more gradual process initiated by vascular injury. Multiple processes, including thrombosis, inflammation, growth factor and cytokine release, cell proliferation, cell migration and extracellular matrix synthesis each contribute to the restenotic process.

While the exact mechanism of restenosis is not completely understood, the general aspects of the restenosis process have been identified. In the normal arterial wall, smooth muscle cells proliferate at a low rate, approximately less than 0.1 percent per day. Smooth muscle cells in the vessel walls exist in a contractile phenotype characterized by eighty to ninety percent of the cell cytoplasmic volume occupied with the contractile apparatus. Endoplasmic reticulum, Golgi, and free ribosomes are few and are located in the perinuclear region. Extracellular matrix surrounds the smooth muscle cells and is rich in heparin-like glycosylaminoglycans which are believed to be responsible for maintaining smooth muscle cells in the contractile phenotypic state (Campbell and Campbell, 1985).

Upon pressure expansion of an intracoronary balloon catheter during angioplasty, smooth muscle cells within the vessel wall become injured, initiating a thrombotic and inflammatory response. Cell derived growth factors such as platelet derived growth factor, fibroblast growth factor, epidermal growth factor, thrombin, etc., released from platelets, invading macrophages and/or leukocytes, or directly from the smooth muscle cells provoke proliferative and migratory responses in medial smooth muscle cells. These cells undergo a change from the contractile phenotype to a synthetic phenotype characterized by only a few contractile filament bundles, extensive rough endoplasmic reticulum, Golgi and free ribosomes. Proliferation/migration usually begins within one to two days post-injury and peaks several days thereafter (Campbell and Campbell, 1987; Clowes and Schwartz, 1985).

Daughter cells migrate to the intimal layer of arterial smooth muscle and continue to proliferate and secrete significant amounts of extracellular matrix proteins. Proliferation, migration and extracellular matrix synthesis continue until the damaged endothelial layer is repaired at which time proliferation slows within the intima, usually within seven to fourteen days post-injury. The newly formed tissue is called neointima. The further vascular narrowing that occurs over the next three to six months is due primarily to negative or constrictive remodeling.

Simultaneous with local proliferation and migration, inflammatory cells invade the site of vascular injury. Within three to seven days post-injury, inflammatory cells have migrated to the deeper layers of the vessel wall. In animal models employing either balloon injury or stent implantation, inflammatory cells may persist at the site of vascular injury for at least thirty days (Tanaka et al., 1993; Edelman et al., 1998). Inflammatory cells therefore are present and may contribute to both the acute and chronic phases of restenosis.

Numerous agents have been examined for presumed anti-proliferative actions in restenosis and have shown some activity in experimental animal models. Some of the agents which have been shown to successfully reduce the extent of intimal hyperplasia in animal models include: heparin and heparin fragments (Clowes, A. W. and Karnovsky M., Nature 265: 25-26, 1977; Guyton, J. R. et al., Circ. Res., 46: 625-634, 1980; Clowes, A. W. and Clowes, M. M., Lab. Invest. 52: 611-616, 1985; Clowes, A. W. and Clowes, M. M., Circ. Res. 58: 839-845, 1986; Majesky et al., Circ. Res. 61: 296-300, 1987; Snow et al., Am. J. Pathol. 137: 313-330, 1990; Okada, T. et al., Neurosurgery 25: 92-98, 1989), colchicine (Currier, J. W. et al., Circ. 80: 11-66, 1989), taxol (Sollot, S. J. et al., J. Clin. Invest. 95: 1869-1876, 1995), angiotensin converting enzyme (ACE) inhibitors (Powell, J. S. et al., Science, 245: 186-188, 1989), angiopeptin (Lundergan, C. F. et al. Am. J. Cardiol. 17(Suppl. B):132B-136B, 1991), cyclosporin A (Jonasson, L. et al., Proc. Natl., Acad. Sci., 85: 2303, 1988), goat-anti-rabbit PDGF antibody (Ferns, G. A. A., et al., Science 253: 1129-1132, 1991), terbinafine (Nemecek, G. M. et al., J. Pharmacol. Exp. Thera. 248: 1167-1174, 1989), trapidil (Liu, M. W. et al., Circ. 81: 1089-1093, 1990), tranilast (Fukuyama, J. et al., Eur. J. Pharmacol. 318: 327-332, 1996), interferon-gamma (Hansson, G. K. and Holm, J., Circ. 84: 1266-1272, 1991), rapamycin (Marx, S. O. et al., Circ. Res. 76: 412-417, 1995), corticosteroids (Colburn, M. D. et al., J. Vasc. Surg. 15:

510-518, 1992), see also Berk, B. C. et al., J. Am. Coll. Cardiol. 17: 111B-117B, 1991), ionizing radiation (Weinberger, J. et al., Int. J. Rad. Onc. Biol. Phys. 36: 767-775, 1996), fusion toxins (Farb, A. et al., Circ. Res. 80: 542-550, 1997) antisense oligonucleotides (Simons, M. et al., Nature 359: 67-70, 1992) and gene vectors (Chang, M. W. et al., J. Clin. Invest. 96: 2260-2268, 1995). Anti-proliferative effects on smooth muscle cells in vitro have been demonstrated for many of these agents, including heparin and heparin conjugates, taxol, tranilast, colchicine, ACE inhibitors, fusion toxins, antisense oligonucleotides, rapamycin and ionizing radiation. Thus, agents with diverse mechanisms of smooth muscle cell inhibition may have therapeutic utility in reducing intimal hyperplasia.

However, in contrast to animal models, attempts in human angioplasty patients to prevent restenosis by systemic pharmacologic means have thus far been unsuccessful. Neither aspirin-dipyridamole, ticlopidine, anti-coagulant therapy (acute heparin, chronic warfarin, hirudin or hirulog), thromboxane receptor antagonism nor steroids have been effective in preventing restenosis, although platelet inhibitors have been effective in preventing acute reocclusion after angioplasty (Mak and Topol, 1997; Lang et al., 1991; Popma et al., 1991). The platelet GP IIb/IIIa receptor, antagonist, Reopro is still under study but has not shown promising results for the reduction in restenosis following angioplasty and stenting. Other agents, which have also been unsuccessful in the prevention of restenosis, include the calcium channel antagonists, prostacyclin mimetics, angiotensin converting enzyme inhibitors, serotonin receptor antagonists, and anti-proliferative agents. These agents must be given systemically, however, and attainment of a therapeutically effective dose may not be possible; anti-proliferative (or anti-restenosis) concentrations may exceed the known toxic concentrations of these agents so that levels sufficient to produce smooth muscle inhibition may not be reached (Mak and Topol, 1997; Lang et al., 1991; Popma et al., 1991).

Additional clinical trials in which the effectiveness for preventing restenosis utilizing dietary fish oil supplements or cholesterol lowering agents has been examined showing either conflicting or negative results so that no pharmacological agents are as yet clinically available to prevent post-angioplasty restenosis (Mak and Topol, 1997; Franklin and Faxon, 1993: Serruys, P. W. et al., 1993). Recent observations suggest that the antilipid/antioxidant agent, probucol may be useful in preventing restenosis but this work requires confirmation (Tardif et al., 1997; Yokoi, et al., 1997). Probucol is presently not approved for use in the United States and a thirty-day pretreatment period would preclude its use in emergency angioplasty. Additionally, the application of ionizing radiation has shown significant promise in reducing or preventing restenosis after angioplasty in patients with stents (Teirstein et al., 1997). Currently, however, the most effective treatments for restenosis are repeat angioplasty, atherectomy or coronary artery bypass grafting, because no therapeutic agents currently have Food and Drug Administration approval for use for the prevention of post-angioplasty restenosis.

Unlike systemic pharmacologic therapy, stents have proven effective in significantly reducing restenosis. Typically, stents are balloon-expandable slotted metal tubes (usually, but not limited to, stainless steel), which, when expanded within the lumen of an angioplastied coronary artery, provide structural support through rigid scaffolding to the arterial wall. This support is helpful in maintaining vessel lumen patency. In two randomized clinical trials, stents increased angiographic success after percutaneous transluminal coronary angioplasty, by increasing minimal lumen diameter and reducing, but not eliminating, the incidence of restenosis at six months (Serruys et al., 1994; Fischman et al., 1994).

Additionally, the heparin coating of stents appears to have the added benefit of producing a reduction in sub-acute thrombosis after stent implantation (Serruys et al., 1996). Thus, sustained mechanical expansion of a stenosed coronary artery with a stent has been shown to provide some measure of restenosis prevention, and the coating of stents with heparin has demonstrated both the feasibility and the clinical usefulness of delivering drugs locally, at the site of injured tissue.

Accordingly, there exists a need for effective drugs and drug delivery systems for the effective prevention and treatment of neointimal thickening that occurs after percutaneous transluminal coronary angioplasty and stent implantation.

SUMMARY OF THE INVENTION

The drugs and drug delivery systems of the present invention provide a means for overcoming the difficulties associated with the methods and devices currently in use as briefly described above.

In accordance with one aspect, the present invention is directed to a method for the prevention of constrictive remodeling. The method comprises the controlled delivery, by release from an intraluminal medical device, of a compound in therapeutic dosage amounts.

In accordance with another aspect, the present invention is directed to a drug delivery device. The drug delivery device comprises an intraluminal medical device and a therapeutic dosage of an agent releasably affixed to the intraluminal medical device for the treatment of constrictive vascular remodeling.

The drugs and drug delivery systems of the present invention utilize a stent or graft in combination with rapamycin or other drugs/agents/compounds to prevent and treat neointimal hyperplasia, i.e. restenosis, following percutaneous transluminal coronary angioplasty and stent implantation. It has been determined that rapamycin functions to inhibit smooth muscle cell proliferation through a number of mechanisms. It has also been determined that rapamycin eluting stent coatings produce superior effects in humans, when compared to animals, with respect to the magnitude and duration of the reduction in neointimal hyperplasia. Rapamycin administration from a local delivery platform also produces an anti-inflammatory effect in the vessel wall that is distinct from and complimentary to its smooth muscle cell anti-proliferative effect. In addition, it has also been demonstrated that rapamycin inhibits constrictive vascular remodeling in humans.

Other drugs, agents or compounds which mimic certain actions of rapamycin may also be utilized in combination with local delivery systems or platforms.

The local administration of drugs, agents or compounds to stented vessels have the additional therapeutic benefit of higher tissue concentration than that which would be achievable through the systemic administration of the same drugs, agents or compounds. Other benefits include reduced systemic toxicity, single treatment, and ease of administration. An additional benefit of a local delivery device and drug, agent or compound therapy may be to reduce the dose of the therapeutic drugs, agents or compounds and thus limit their toxicity, while still achieving a reduction in restenosis.

BRIEF DESCRIPTION OF THE DRAWINGS

The foregoing and other features and advantages of the invention will be apparent from the following, more particular description of preferred embodiments of the invention, as illustrated in the accompanying drawings.

DETAILED DESCRIPTION OF THE PREFERRED EMBODIMENTS

Figure 1:
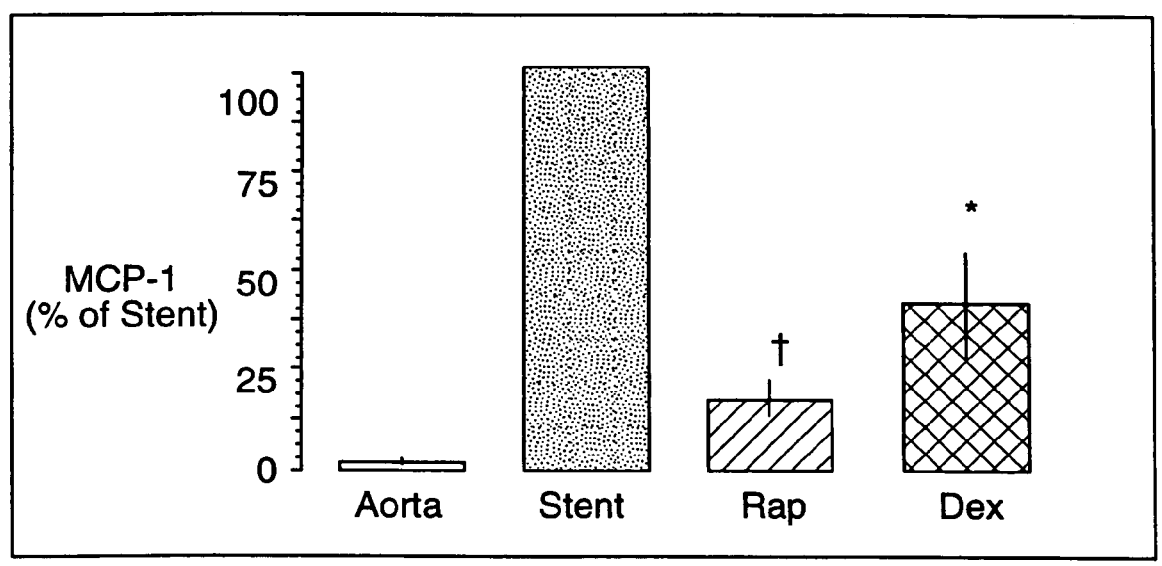
FIG. 1 is a chart indicating the effectiveness of rapamycin as an anti-inflammatory relative to other anti-inflammatories.

As stated above, the proliferation of vascular smooth muscle cells in response to mitogenic stimuli that are released during balloon angioplasty and stent implantation is the primary cause of neointimal hyperplasia. Excessive neointimal hyperplasia can often lead to impairment of blood flow, cardiac ischemia and the need for a repeat intervention in selected patients in high risk treatment groups. Yet repeat revascularization incurs risk of patient morbidity and mortality while adding significantly to the cost of health care. Given the widespread use of stents in interventional practice, there is a clear need for safe and effective inhibitors of neointimal hyperplasia.

Rapamycin is a macroyclic triene antibiotic produced by streptomyces hygroscopicus as disclosed in U.S. Pat. No. 3,929,992. It has been found that rapamycin inhibits the proliferation of vascular smooth muscle cells in vivo. Accordingly, rapamycin may be utilized in treating intimal smooth muscle cell hyperplasia, restenosis and vascular occlusion in a mammal, particularly following either biologically or mechanically mediated vascular injury, or under conditions that would predispose a mammal to suffering such a vascular injury. Rapamycin functions to inhibit smooth muscle cell proliferation and does not interfere with the re-endothelialization of the vessel walls.

Rapamycin functions to inhibit smooth muscle cell proliferation through a number of mechanisms. In addition, rapamycin reduces the other effects caused by vascular injury, for example, inflammation. The operation and various functions of rapamycin are described in detail below. Rapamycin as used throughout this application shall include rapamycin, rapamycin analogs, derivatives and congeners that bind FKBP12 and possess the same pharmacologic properties as rapamycin.

Rapamycin reduces vascular hyperplasia by antagonizing smooth muscle proliferation in response to mitogenic signals that are released during angioplasty. Inhibition of growth factor and cytokine mediated smooth muscle proliferation at the late G1 phase of the cell cycle is believed to be the dominant mechanism of action of rapamycin. However, rapamycin is also known to prevent T-cell proliferation and differentiation when administered systemically. This is the basis for its immunosuppresive activity and its ability to prevent graft rejection.

The molecular events that are responsible for the actions of rapamycin, a known anti-proliferative, which acts to reduce the magnitude and duration of neointimal hyperplasia, are still being elucidated. It is known, however, that rapamycin enters cells and binds to a high-affinity cytosolic protein called FKBP12. The complex of rapamycin and FKPB12 in turn binds to and inhibits a phosphoinositide (PI)-3 kinase called the "mammalian Target of Rapamycin" or TOR. TOR is a protein kinase that plays a key role in mediating the downstream signaling events associated with mitogenic growth factors and cytokines in smooth muscle cells and T lymphocytes. These events include phosphorylation of p27, phosphorylation of p70 s6 kinase and phosphorylation of 4BP-1, an important regulator of protein translation.

It is recognized that rapamycin reduces restenosis by inhibiting neointimal hyperplasia. However, there is evidence that rapamycin may also inhibit the other major component of restenosis, namely, negative remodeling. Remodeling is a process whose mechanism is not clearly understood but which results in shrinkage of the external elastic lamina and reduction in lumenal area over time, generally a period of approximately three to six months in humans.

Negative or constrictive vascular remodeling may be quantified angiographically as the percent diameter stenosis at the lesion site where there is no stent to obstruct the process. If late lumen loss is abolished in-lesion, it may be inferred that negative remodeling has been inhibited. Another method of determining the degree of remodeling involves measuring in-lesion external elastic lamina area using intravascular ultrasound (IVUS). Intravascular ultrasound is a technique that can image the external elastic lamina as well as the vascular lumen. Changes in the external elastic lamina proximal and distal to the stent from the post-procedural timepoint to four-month and twelve-month follow-ups are reflective of remodeling changes.

Evidence that rapamycin exerts an effect on remodeling comes from human implant studies with rapamycin coated stents showing a very low degree of restenosis in-lesion as well as in-stent. In-lesion parameters are usually measured approximately five millimeters on either side of the stent i.e. proximal and distal. Since the stent is not present to control remodeling in these zones which are still affected by balloon expansion, it may be inferred that rapamycin is preventing vascular remodeling.

The data in Table 1 below illustrate that in-lesion percent diameter stenosis remains low in the rapamycin treated groups, even at twelve months. Accordingly, these results support the hypothesis that rapamycin reduces remodeling.

TABLE 1.0

Angiographic In-Lesion Percent Diameter Stenosis (%, mean ± SD and "n=") In Patients Who Received a Rapamycin-Coated Stent

| Coating Group | Post Placement | 4–6 month Follow Up | 12 month Follow Up |
|---|---|---|---|
| Brazil | 10.6 ± 5.7 (30) | 13.6 ± 8.6 (30) | 22.3 ± 7.2 (15) |
| Netherlands | 14.7 ± 8.8 | 22.4 ± 6.4 | — |

Additional evidence supporting a reduction in negative remodeling with rapamycin comes from intravascular ultrasound data that was obtained from a first-in-man clinical program as illustrated in Table 2 below.

TABLE 2.0

Matched IVUS data in Patients Who Received a Rapamycin-Coated Stent

| IVUS Parameter | Post (n=) | 4-Month Follow-Up (n=) | 12-Month Follow-Up (n=) |
|---|---|---|---|
| Mean proximal vessel area (mm$^2$) | 16.53 ± 3.53 (27) | 16.31 ± 4.36 (28) | 13.96 ± 2.26 (13) |
| Mean distal vessel area (mm$^2$) | 13.12 ± 3.68 (26) | 13.53 ± 4.17 (26) | 12.49 ± 3.25 (14) |

The data illustrated that there is minimal loss of vessel area proximally or distally which indicates that inhibition of negative remodeling has occurred in vessels treated with rapamycin-coated stents.

Other than the stent itself, there have been no effective solutions to the problem of vascular remodeling. Accordingly, rapamycin may represent a biological approach to controlling the vascular remodeling phenomenon.

It may be hypothesized that rapamycin acts to reduce negative remodeling in several ways. By specifically blocking the proliferation of fibroblasts in the vascular wall in response to injury, rapamycin may reduce the formation of vascular scar tissue. Rapamycin may also affect the translation of key proteins involved in collagen formation or metabolism.

Rapamycin used in this context includes rapamycin and all analogs, derivatives and congeners that bind FKBP12 and possess the same pharmacologic properties as rapamycin.

In a preferred embodiment, the rapamycin is delivered by a local delivery device to control negative remodeling of an arterial segment after balloon angioplasty as a means of reducing or preventing restenosis. While any delivery device may be utilized, it is preferred that the delivery device comprises a stent that includes a coating or sheath which elutes or releases rapamycin. The delivery system for such a device may comprise a local infusion catheter that delivers rapamycin at a rate controlled by the administrator.

Rapamycin may also be delivered systemically using an oral dosage form or a chronic injectible depot form or a patch to deliver rapamycin for a period ranging from about seven to forty-five days to achieve vascular tissue levels that are sufficient to inhibit negative remodeling. Such treatment is to be used to reduce or prevent restenosis when administered several days prior to elective angioplasty with or without a stent.

Data generated in porcine and rabbit models show that the release of rapamycin into the vascular wall from a nonerodible polymeric stent coating in a range of doses (35-430 ug/5-18 mm coronary stent) produces a peak fifty to fifty-five percent reduction in neointimal hyperplasia as set forth in Table 3 below. This reduction, which is maximal at about twenty-eight to thirty days, is typically not sustained in the range of ninety to one hundred eighty days in the porcine model as set forth in Table 4 below.

TABLE 3.0

Animal Studies with Rapamycin-coated stents.
Values are mean ± Standard Error of Mean

| Study | Duration | Stent[1] | Rapamycin | N | Neointimal Area (mm$^2$) | % Change From Polyme | % Change From Metal |
|---|---|---|---|---|---|---|---|
| Porcine | | | | | | | |
| 98009 | 14 days | Metal | | 8 | 2.04 ± 0.17 | | |
| | | 1X + rapamycin | 153 μg | 8 | 1.66 ± 0.17* | −42% | −19% |
| | | 1X + TC300 + rapamycin | 155 μg | 8 | 1.51 ± 0.19* | −47% | −26% |
| 99005 | 28 days | Metal | | 10 | 2.29 ± 0.21 | | |
| | | | | 9 | 3.91 ± 0.60** | | |
| | | 1X + TC30 + rapamycin | 130 μg | 8 | 2.81 ± 0.34 | | +23% |
| | | 1X + TC100 + rapamycin | 120 μg | 9 | 2.62 ± 0.21 | | +14% |
| 99006 | 28 days | Metal | | 12 | 4.57 ± 0.46 | | |
| | | EVA/BMA 3X | | 12 | 5.02 ± 0.62 | | +10% |
| | | 1X + rapamycin | 125 μg | 11 | 2.84 ± 0.31* ** | −43% | −38% |
| | | 3X + rapamycin | 430 μg | 12 | 3.06 ± 0.17* ** | −39% | −33% |
| | | 3X + rapamycin | 157 μg | 12 | 2.77 ± 0.41* ** | −45% | −39% |
| 99011 | 28 days | Metal | | 11 | 3.09 ± 0.27 | | |
| | | | | 11 | 4.52 ± 0.37 | | |
| | | 1X + rapamycin | 189 μg | 14 | 3.05 ± 0.35 | | −1% |
| | | 3X + rapamycin/dex | 182/363 μg | 14 | 2.72 ± 0.71 | | −12% |
| 99021 | 60 days | Metal | | 12 | 2.14 ± 0.25 | | |
| | | 1X + rapamycin | 181 μg | 12 | 2.95 ± 0.38 | | +38% |
| 99034 | 28 days | Metal | | 8 | 5.24 ± 0.58 | | |
| | | 1X + rapamycin | 186 μg | 8 | 2.47 ± 0.33** | | −53% |
| | | 3X + rapamycin/dex | 185/369 μg | 6 | 2.42 ± 0.64** | | −54% |
| 20001 | 28 days | Metal | | 6 | 1.81 ± 0.09 | | |
| | | 1X + rapamycin | 172 μg | 5 | 1.66 ± 0.44 | | −8% |
| 20007 | 30 days | Metal | | 9 | 2.94 ± 0.43 | | |
| | | 1XTC + rapamycin | 155 μg | 10 | 1.40 ± 0.11* | | −52%* |
| Rabbit | | | | | | | |
| 99019 | 28 days | Metal | | 8 | 1.20 ± 0.07 | | |

TABLE 3.0-continued

Animal Studies with Rapamycin-coated stents.
Values are mean ± Standard Error of Mean

| Study | Duration | Stent[1] | Rapamycin | N | Neointimal Area (mm²) | % Change From Polyme | % Change From Metal |
|---|---|---|---|---|---|---|---|
| | | EVA/BMA 1X | | 10 | 1.26 ± 0.16 | | +5% |
| | | 1X + rapamycin | 64 µg | 9 | 0.92 ± 0.14 | −27% | −23% |
| | | 1X + rapamycin | 196 µg | 10 | 0.66 ± 0.12* ** | −48% | −45% |
| 99020 | 28 days | Metal | | 12 | 1.18 ± 0.10 | | |
| | | EVA/BMA 1X + rapamycin | 197 µg | 8 | 0.81 ± 0.16 | | −32% |

[1]Stent nomenclature: EVA/BMA 1X, 2X, and 3X signifies approx. 500 µg, 1000 µg, and 1500 µg total mass (polymer + drug), respectively. TC, top coat of 30 µg, 100 µg, or 300 µg drug-free BMA; Biphasic; 2 × 1X layers of rapamycin in EVA/BMA spearated by a 100 µg drug-free BMA layer.
[2]0.25 mg/kg/d × 14 d preceeded by a loading dose of 0.5 mg/kg/d × 3 d prior to stent implantation.
*p < 0.05 from EVA/BMA control.
**p < 0.05 from Metal;
Inflammation score: (0 = essentially no intimal involvement; 1 = <25% intima involved; 2 = ≧25% intima involved; 3 = >50% intima involved).

TABLE 4.0

180 day Porcine Study with Rapamycin-coated stents.
Values are mean ± Standard Error of Mean

| Study | Duration | Stent[1] | Rapamycin | N | Neointimal Area (mm²) | % Change From Polyme | % Change From Metal | Inflammation Score # |
|---|---|---|---|---|---|---|---|---|
| 20007 | 3 days | Metal | | 10 | 0.38 ± 0.06 | | | 1.05 ± 0.06 |
| (ETP-2-002233-P) | | 1XTC + rapamycin | 155 µg | 10 | 0.29 ± 0.03 | | −24% | 1.08 ± 0.04 |
| | 30 days | Metal | | 9 | 2.94 ± 0.43 | | | 0.11 ± 0.08 |
| | | 1XTC + rapamycin | 155 µg | 10 | 1.40 ± 0.11* | | −52%* | 0.25 ± 0.10 |
| | 90 days | Metal | | 10 | 3.45 ± 0.34 | | | 0.20 ± 0.08 |
| | | 1XTC + rapamycin | 155 µg | 10 | 3.03 ± 0.29 | | −12% | 0.80 ± 0.23 |
| | | 1X + rapamycin | 171 µg | 10 | 2.86 ± 0.35 | | −17% | 0.60 ± 0.23 |
| | 180 days | Metal | | 10 | 3.65 ± 0.39 | | | 0.65 ± 0.21 |
| | | 1XTC + rapamycin | 155 µg | 10 | 3.34 ± 0.31 | | −8% | 1.50 ± 0.34 |
| | | 1X + rapamycin | 171 µg | 10 | 3.87 ± 0.28 | | +6% | 1.68 ± 0.37 |

The release of rapamycin into the vascular wall of a human from a nonerodible polymeric stent coating provides superior results with respect to the magnitude and duration of the reduction in neointimal hyperplasia within the stent as compared to the vascular walls of animals as set forth above.

Humans implanted with a rapamycin coated stent comprising rapamycin in the same dose range as studied in animal models using the same polymeric matrix, as described above, reveal a much more profound reduction in neointimal hyperplasia than observed in animal models, based on the magnitude and duration of reduction in neointima. The human clinical response to rapamycin reveals essentially total abolition of neointimal hyperplasia inside the stent using both angiographic and intravascular ultrasound measurements. These results are sustained for at least one year as set forth in Table 5 below.

TABLE 5.0

Patients Treated (N = 45 patients) with a Rapamycin-coated Stent

| Effectiveness Measures | Sirolimus FIM (N = 45 Patients, 45 Lesions) | 95% Confidence Limit |
|---|---|---|
| Procedure Success (QCA) | 100.0% (45/45) | [92.1%, 100.0%] |
| 4-month In-Stent Diameter Stenosis (%) | | |
| Mean ± SD (N) | 4.8% ± 6.1% (30) | [2.6%, 7.0%] |
| Range (min, max) | (−8.2%, 14.9%) | |
| 6-month In-Stent Diameter Stenosis (%) | | |
| Mean ± SD (N) | 8.9% ± 7.6% (13) | [4.8%, 13.0%] |
| Range (min, max) | (−2.9%, 20.4%) | |
| 12-month In-Stent Diameter Stenosis (%) | | |
| Mean ± SD (N) | 8.9% ± 6.1% (15) | [5.8%, 12.0%] |
| Range (min, max) | (−3.0%, 22.0%) | |

TABLE 5.0-continued

Patients Treated (N = 45 patients) with a Rapamycin-coated Stent

| Effectiveness Measures | Sirolimus FIM (N = 45 Patients, 45 Lesions) | 95% Confidence Limit |
|---|---|---|
| 4-month In-Stent Late Loss (mm) | | |
| Mean ± SD (N) | 0.00 ± 0.29 (30) | [−0.10, 0.10] |
| Range (min, max) | (−0.51, 0.45) | |
| 6-month In-Stent Late Loss (mm) | | |
| Mean ± SD (N) | 0.25 ± 0.27 (13) | [0.10, 0.39] |
| Range (min, max) | (−0.51, 0.91) | |
| 12-month In-Stent Late Loss (mm) | | |
| Mean ± SD (N) | 0.11 ± 0.36 (15) | [−0.08, 0.29] |
| Range (min, max) | (−0.51, 0.82) | |
| 4-month Obstruction Volume (%) (IVUS) | | |
| Mean ± SD (N) | 10.48% ± 2.78% (28) | [9.45%, 11.51%] |
| Range (min, max) | (4.60%, 16.35%) | |
| 6-month Obstruction Volume (%) (IVUS) | | |
| Mean ± SD (N) | 7.22% ± 4.60% (13) | [4.72%, 9.72%], |
| Range (min, max) | (3.82%, 19.88%) | |
| 12-month Obstruction Volume (%) (IVUS) | | |
| Mean ± SD (N) | 2.11% ± 5.28% (15) | [0.00%, 4.78%], |
| Range (min, max) | (0.00%, 19.89%) | |
| 6-month Target Lesion Revascularization (TLR) | 0.0% (0/30) | [0.0%, 9.5%] |
| 12-month Target Lesion Revascularization (TLR) | 0.0% (0/15) | [0.0%, 18.1%] |

QCA = Quantitative Coronary Angiography
SD = Standard Deviation
IVUS = Intravascular Ultrasound Rapamycin produces an unexpected benefit in humans when delivered from a stent by causing a profound reduction in in-stent neointimal hyperplasia that is sustained for at least one year. The magnitude and duration of this benefit in humans is not predicted from animal model data. Rapamycin used in this context includes rapamycin and all analogs, derivatives and congeners that bind FKBP12 and possess the same pharmacologic properties as rapamycin.

These results may be due to a number of factors. For example, the greater effectiveness of rapamycin in humans is due to greater sensitivity of its mechanism(s) of action toward the pathophysiology of human vascular lesions compared to the pathophysiology of animal models of angioplasty. In addition, the combination of the dose applied to the stent and the polymer coating that controls the release of the drug is important in the effectiveness of the drug.

As stated above, rapamycin reduces vascular hyperplasia by antagonizing smooth muscle proliferation in response to mitogenic signals that are released during angioplasty injury. Also, it is known that rapamycin prevents T-cell proliferation and differentiation when administered systemically. It has also been determined that rapamycin exerts a local inflammatory effect in the vessel wall when administered from a stent in low doses for a sustained period of time (approximately two to six weeks). The local anti-inflammatory benefit is profound and unexpected. In combination with the smooth muscle anti-proliferative effect, this dual mode of action of rapamycin may be responsible for its exceptional efficacy.

Accordingly, rapamycin delivered from a local device platform, reduces neointimal hyperplasia by a combination of anti-inflammatory and smooth muscle anti-proliferative effects. Rapamycin used in this context means rapamycin and all analogs, derivatives and congeners that bind FKBP12 and possess the same pharmacologic properties as rapamycin. Local device platforms include stent coatings, stent sheaths, grafts and local drug infusion catheters or porous balloons or any other suitable means for the in situ or local delivery of drugs, agents or compounds.

The anti-inflammatory effect of rapamycin is evident in data from an experiment, illustrated in Table 6, in which rapamycin delivered from a stent was compared with dexamethasone delivered from a stent. Dexamethasone, a potent steroidal anti-inflammatory agent, was used as a reference standard. Although dexamethasone is able to reduce inflammation scores, rapamycin is far more effective than dexamethasone in reducing inflammation scores. In addition, rapamycin significantly reduces neointimal hyperplasia, unlike dexamethasone.

TABLE 6.0

| Group Rapamycin Rap | N= | Neointimal Area (mm²) | % Area Stenosis | Inflammation Score |
|---|---|---|---|---|
| Uncoated | 8 | 5.24 ± 1.65 | 54 ± 19 | 0.97 ± 1.00 |
| Dexamethasone (Dex) | 8 | 4.31 ± 3.02 | 45 ± 31 | 0.39 ± 0.24 |
| Rapamycin (Rap) | 7 | 2.47 ± 0.94* | 26 ± 10* | 0.13 ± 0.19* |
| Rap + Dex | 6 | 2.42 ± 1.58* | 26 ± 18* | 0.17 ± 0.30* |

*= significance level P < 0.05

Rapamycin has also been found to reduce cytokine levels in vascular tissue when delivered from a stent. The data in FIG. 1 illustrates that rapamycin is highly effective in reducing monocyte chemotactic protein (MCP-1) levels in the vascular wall. MCP-1 is an example of a proinflammatory/chemotactic cytokine that is elaborated during vessel injury. Reduction in MCP-1 illustrates the beneficial effect of rapamycin in reducing the expression of proinflammatory mediators and contributing to the anti-inflammatory effect of rapamycin delivered locally from a stent. It is recognized that vascular inflammation in response to injury is a major contributor to the development of neointimal hyperplasia.

Since rapamycin may be shown to inhibit local inflammatory events in the vessel it is believed that this could explain the unexpected superiority of rapamycin in inhibiting neointima.

As set forth above, rapamycin functions on a number of levels to produce such desired effects as the prevention of T-cell proliferation, the inhibition of negative remodeling, the reduction of inflammation, and the prevention of smooth muscle cell proliferation. While the exact mechanisms of these functions are not completely known, the mechanisms that have been identified may be expanded upon.

Studies with rapamycin suggest that the prevention of smooth muscle cell proliferation by blockade of the cell cycle is a valid strategy for reducing neointimal hyperplasia. Dramatic and sustained reductions in late lumen loss and neointimal plaque volume have been observed in patients receiving rapamycin delivered locally from a stent. The present invention expands upon the mechanism of rapamycin to include additional approaches to inhibit the cell cycle and reduce neointimal hyperplasia without producing toxicity.

The cell cycle is a tightly controlled biochemical cascade of events that regulate the process of cell replication. When cells are stimulated by appropriate growth factors, they move from $G_0$ (quiescence) to the G1 phase of the cell cycle. Selective inhibition of the cell cycle in the G1 phase, prior to DNA replication (S phase), may offer therapeutic advantages of cell preservation and viability while retaining anti-proliferative efficacy when compared to therapeutics that act later in the cell cycle i.e. at S, G2 or M phase.

Accordingly, the prevention of intimal hyperplasia in blood vessels and other conduit vessels in the body may be achieved using cell cycle inhibitors that act selectively at the G1 phase of the cell cycle. These inhibitors of the G1 phase of the cell cycle may be small molecules, peptides, proteins, oligonucleotides or DNA sequences. More specifically, these drugs or agents include inhibitors of cyclin dependent kinases (cdk's) involved with the progression of the cell cycle through the G1 phase, in particular cdk2 and cdk4.

Examples of drugs, agents or compounds that act selectively at the G1 phase of the cell cycle include small molecules such as flavopiridol and its structural analogs that have been found to inhibit cell cycle in the late G1 phase by antagonism of cyclin dependent kinases. Therapeutic agents that elevate an endogenous kinase inhibitory protein$^{kip}$ called P27, sometimes referred to as P27$^{kip1}$, that selectively inhibits cyclin dependent kinases may be utilized. This includes small molecules, peptides and proteins that either block the degradation of P27 or enhance the cellular production of P27, including gene vectors that can transfact the gene to produce P27. Staurosporin and related small molecules that block the cell cycle by inhibiting protein kinases may be utilized. Protein kinase inhibitors, including the class of tyrphostins that selectively inhibit protein kinases to antagonize signal transduction in smooth muscle in response to a broad range of growth factors such as PDGF and FGF may also be utilized.

Any of the drugs, agents or compounds discussed above may be administered either systemically, for example, orally, intravenously, intramuscularly, subcutaneously, nasally or intradermally, or locally, for example, stent coating, stent covering or local delivery catheter. In addition, the drugs or agents discussed above may be formulated for fast-release or slow release with the objective of maintaining the drugs or agents in contact with target tissues for a period ranging from three days to eight weeks.

As set forth above, the complex of rapamycin and FKPB12 binds to and inhibits a phosphoinositide (PI)-3 kinase called the mammalian Target of Rapamycin or TOR. An antagonist of the catalytic activity of TOR, functioning as either an active site inhibitor or as an allosteric modulator, i.e. an indirect inhibitor that allosterically modulates, would mimic the actions of rapamycin but bypass the requirement for FKBP12. The potential advantages of a direct inhibitor of TOR include better tissue penetration and better physical/chemical stability. In addition, other potential advantages include greater selectivity and specificity of action due to the specificity of an antagonist for one of multiple isoforms of TOR that may exist in different tissues, and a potentially different spectrum of downstream effects leading to greater drug efficacy and/or safety.

The inhibitor may be a small organic molecule (approximate mw<1000), which is either a synthetic or naturally derived product. Wortmanin may be an agent which inhibits the function of this class of proteins. It may also be a peptide or an oligonucleotide sequence. The inhibitor may be administered either sytemically (orally, intravenously, intramuscularly, subcutaneously, nasally, or intradermally) or locally (stent coating, stent covering, local drug delivery catheter). For example, the inhibitor may be released into the vascular wall of a human from a nonerodible polymeric stent coating. In addition, the inhibitor may be formulated for fast-release or slow release with the objective of maintaining the rapamycin or other drug, agent or compound in contact with target tissues for a period ranging from three days to eight weeks.

As stated previously, the implantation of a coronary stent in conjunction with balloon angioplasty is highly effective in treating acute vessel closure and may reduce the risk of restenosis. Intravascular ultrasound studies (Mintz et al., 1996) suggest that coronary stenting effectively prevents vessel constriction and that most of the late luminal loss after stent implantation is due to plaque growth, probably related to neointimal hyperplasia. The late luminal loss after coronary stenting is almost two times higher than that observed after conventional balloon angioplasty. Thus, inasmuch as stents prevent at least a portion of the restenosis process, the use of drugs, agents or compounds which prevent inflammation and proliferation, or prevent proliferation by multiple mechanisms, combined with a stent may provide the most efficacious treatment for post-angioplasty restenosis.

The local delivery of drugs, agents or compounds from a stent has the following advantages; namely, the prevention of vessel recoil and remodeling through the scaffolding action of the stent and the drugs, agents or compounds and the prevention of multiple components of neointimal hyperplasia. This local administration of drugs, agents or compounds to stented coronary arteries may also have additional therapeutic benefit. For example, higher tissue concentrations would be achievable than that which would occur with systemic administration, reduced systemic toxicity, and single treatment and ease of administration. An additional benefit of drug therapy may be to reduce the dose of the therapeutic compounds, thereby limiting their toxicity, while still achieving a reduction in restenosis.

There are a multiplicity of different stents that may be utilized following percutaneous transluminal coronary angioplasty. Although any number of stents may be utilized in accordance with the present invention, for simplicity, one particular stent will be described in exemplary embodiments of the present invention. The skilled artisan will recognize that any number of stents may be utilized in connection with the present invention.

A stent is commonly used as a tubular structure left inside the lumen of a duct to relieve an obstruction. Commonly, stents are inserted into the lumen in a non-expanded form and are then expanded autonomously, or with the aid of a second device in situ. A typical method of expansion occurs through the use of a catheter-mounted angioplasty balloon which is inflated within the stenosed vessel or body passageway in order to shear and disrupt the obstructions associated with the wall components of the vessel and to obtain an enlarged lumen. As set forth below, self-expanding stents may also be utilized.

Figure 2:
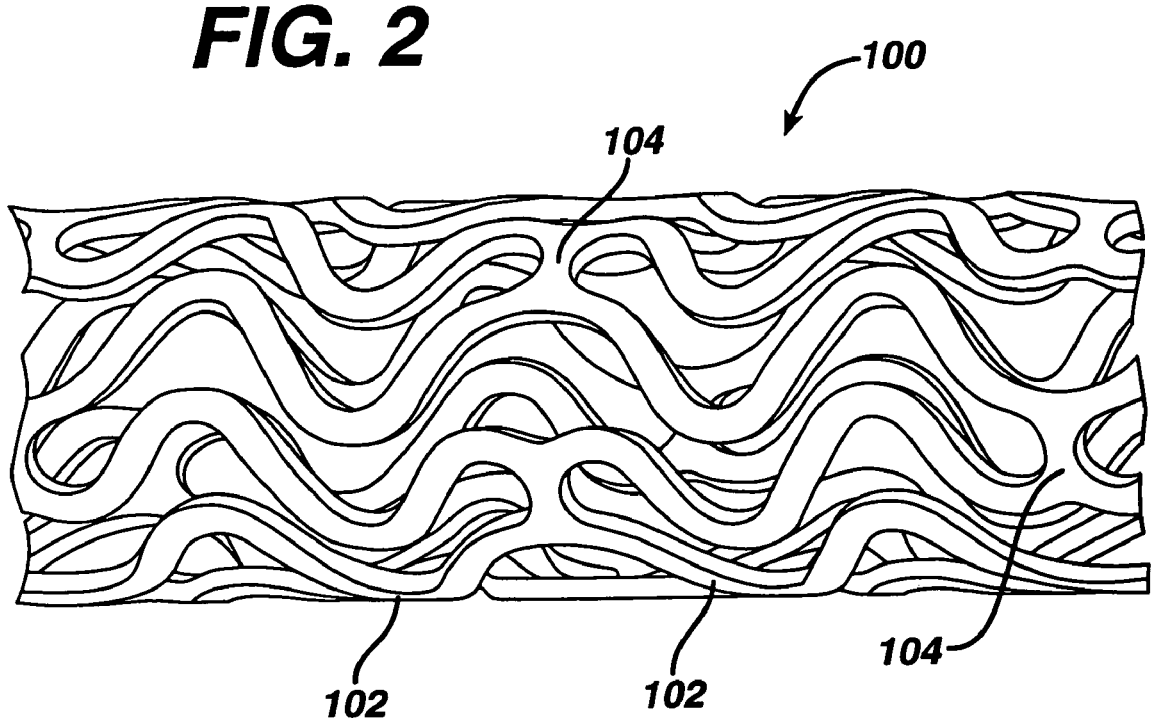
FIG. 2 is a view along the length of a stent (ends not shown) prior to expansion showing the exterior surface of the stent and the characteristic banding pattern.

FIG. 2 illustrates an exemplary stent 100 which may be utilized in accordance with an exemplary embodiment of the present invention. The expandable cylindrical stent 100 comprises a fenestrated structure for placement in a blood vessel, duct or lumen to hold the vessel, duct or lumen open, more particularly for protecting a segment of artery from restenosis after angioplasty. The stent 100 may be expanded circumferentially and maintained in an expanded configuration, that is circumferentially or radially rigid. The stent 100 is axially flexible and when flexed at a band, the stent 100 avoids any externally-protruding component parts.

The stent 100 generally comprises first and second ends with an intermediate section therebetween. The stent 100 has a longitudinal axis and comprises a plurality of longitudinally disposed bands 102, wherein each band 102 defines a generally continuous wave along a line segment parallel to the longitudinal axis. A plurality of circumferentially arranged links 104 maintain the bands 102 in a substantially tubular structure. Essentially, each longitudinally disposed band 102 is connected at a plurality of periodic locations, by a short circumferentially arranged link 104 to an adjacent band 102. The wave associated with each of the bands 102 has approximately the same fundamental spatial frequency in the intermediate section, and the bands 102 are so disposed that the wave associated with them are generally aligned so as to be generally in phase with one another. As illustrated in the figure, each longitudinally arranged band 102 undulates through approximately two cycles before there is a link to an adjacent band.

The stent 100 may be fabricated utilizing any number of methods. For example, the stent 100 may be fabricated from a hollow or formed stainless steel tube that may be machined using lasers, electric discharge milling, chemical etching or other means. The stent 100 is inserted into the body and placed at the desired site in an unexpanded form. In one embodiment, expansion may be effected in a blood vessel by a balloon catheter, where the final diameter of the stent 100 is a function of the diameter of the balloon catheter used.

It should be appreciated that a stent 100 in accordance with the present invention may be embodied in a shape-memory material, including, for example, an appropriate alloy of nickel and titanium. In this embodiment, after the stent 100 has been formed it may be compressed so as to occupy a space sufficiently small as to permit its insertion in a blood vessel or other tissue by insertion means, wherein the insertion means include a suitable catheter, or flexible rod. On emerging from the catheter, the stent 100 may be configured to expand into the desired configuration where the expansion is automatic or triggered by a change in pressure, temperature or electrical stimulation.

Figure 3:
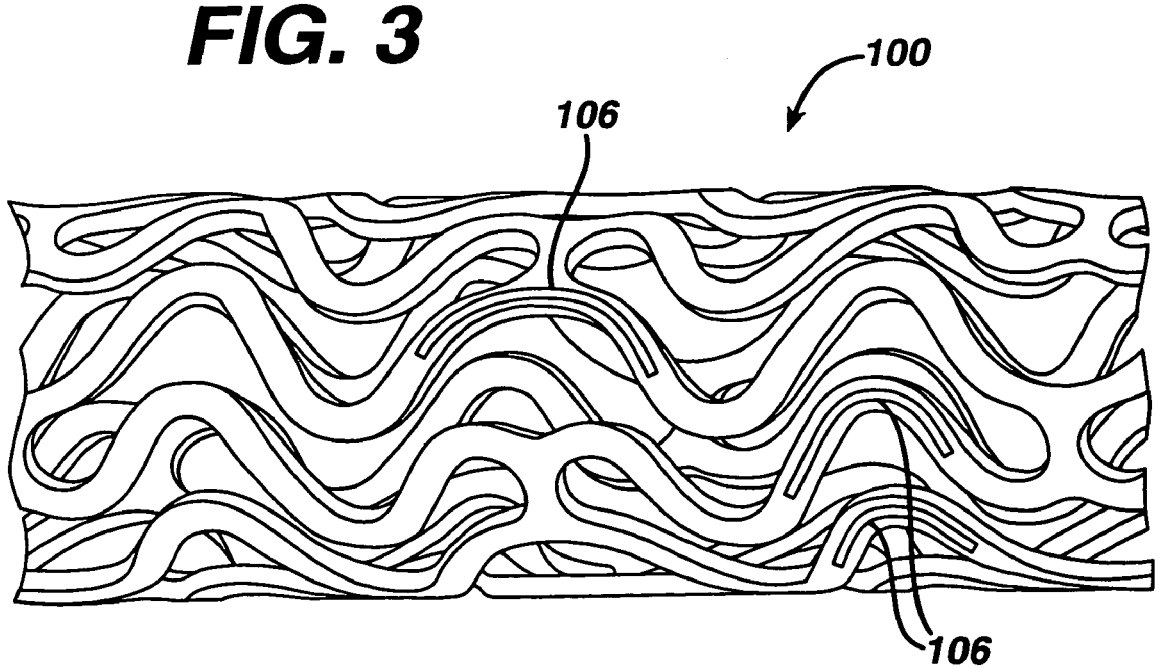
FIG. 3 is a perspective view of the stent of FIG. 1 having reservoirs in accordance with the present invention.

FIG. 3 illustrates an exemplary embodiment of the present invention utilizing the stent 100 illustrated in FIG. 2. As illustrated, the stent 100 may be modified to comprise a reservoir 106. Each of the reservoirs may be opened or closed as desired. These reservoirs 106 may be specifically designed to hold the drug, agent, compound or combinations thereof to be delivered. Regardless of the design of the stent 100, it is preferable to have the drug, agent, compound or combinations thereof dosage applied with enough specificity and a sufficient concentration to provide an effective dosage in the lesion area. In this regard, the reservoir size in the bands 102 is preferably sized to adequately apply the drug/drug combination dosage at the desired location and in the desired amount.

In an alternate exemplary embodiment, the entire inner and outer surface of the stent 100 may be coated with various drug and drug combinations in therapeutic dosage amounts. A detailed description of exemplary coating techniques is described below.

Rapamycin or any of the drugs, agents or compounds described above may be incorporated into or affixed to the stent in a number of ways and utilizing any number of biocompatible materials. In the exemplary embodiment, the rapamycin is directly incorporated into a polymeric matrix and sprayed onto the outer surface of the stent. The rapamycin elutes from the polymeric matrix over time and enters the surrounding tissue. The rapamycin preferably remains on the stent for at least three days up to approximately six months and more preferably between seven and thirty days.

Any number of non-erodible polymers may be utilized in conjunction with rapamycin. In the exemplary embodiment, the polymeric matrix comprises two layers. The base layer comprises a solution of ethylene-co-vinylacetate and polybutylmethacrylate. The rapamycin is incorporated into this layer. The outer layer comprises only polybutylmethacrylate and acts as a diffusion barrier to prevent the rapamycin from eluting too quickly and entering the surrounding tissues. The thickness of the outer layer or top coat determines the rate at which the rapamycin elutes from the matrix. Essentially, the rapamycin elutes from the matrix by diffusion through the polymer molecules. Polymers tend to move, thereby allowing solids, liquids and gases to escape therefrom. The total thickness of the polymeric matrix is in the range from about 1 micron to about 20 microns or greater. In a preferred exemplary embodiment, the base layer, including the polymer and drug, has a thickness in the range from about 8 microns to about 12 microns and the outer layer has a thickness in the range from about 1 micron to about 2 microns.

The ethylene-co-vinylacetate, polybutylmethacrylate and rapamycin solution may be incorporated into or onto the stent in a number of ways. For example, the solution may be sprayed onto the stent or the stent may be dipped into the solution. In a preferred embodiment, the solution is sprayed onto the stent and then allowed to dry. In another exemplary embodiment, the solution may be electrically charged to one polarity and the stent electrically changed to the opposite polarity. In this manner, the solution and stent will be attracted to one another. In using this type of spraying process, waste may be reduced and more control over the thickness of the coat may be achieved.

Since rapamycin works by entering the surrounding tissue, it is preferably only affixed to the surface of the stent making contact with one tissue. Typically, only the outer surface of the stent makes contact with the tissue. Accordingly, in a preferred embodiment, only the outer surface of the stent is coated with rapamycin. For other drugs, agents or compounds, the entire stent may be coated.

It is important to note that different polymers may be utilized for different stents. For example, in the above-described embodiment, ethylene-co-vinylacetate and polybutylmethacrylate are utilized to form the polymeric matrix. This matrix works well with stainless steel stents. Other polymers may be utilized more effectively with stents formed from other materials, including materials that exhibit superelastic properties such as alloys of nickel and titanium.

Although shown and described is what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope of the appended claims.

What is claimed is:

1. A drug delivery device comprising: an intraluminal stent; a biocompatible, nonerodible polymeric coating affixed to the intraluminal stent; and from about 64 μg to about 197 μg of rapamycin or a macrocyclic triene analog thereof that binds FKBP12 incorporated into the polymeric coating, wherein said device provides an in-stent late loss in diameter at 12 months following implantation in a human of less than about 0.5 mm, as measured by quantitative coronary angiography.

2. A drug delivery device according to claim 1 that provides an in- stent late loss in diameter at 12 months following implantation in a human of less than about 0.3 mm, as measured by quantitative coronary angiography.

3. A drug delivery device according to claim 1 or 2 that provides an in-stent diameter stenosis at 12 months following implantation in a human of less than about 22%, as measured by quantitative coronary angiography.

4. A drug delivery device according to claim 3 that provides an in-stent diameter stenosis at 12 months following implantation in a human of less than about 15%, as measured by quantitative coronary angiography.

5. A drug delivery device comprising: an intraluminal stent; a biocompatible, nonerodible polymeric coating affixed to the intraluminal stent; and from about 64 μg to about 197 μg of rapamycin or a macrocyclic triene analog thereof that binds FKBP12 incorporated into the polymeric coating, wherein said device provides a mean in-stent late loss in diameter in a human population at 12 months following implantation of less than about 0.5 mm, as measured by quantitative coronary angiography.

6. A drug delivery device according to claim 5 that provides a mean in-stent late loss in diameter in a human population at 12 months following implantation of less than about 0.3 mm, as measured by quantitative coronary angiography.

7. A drug delivery device according to claim 5 or 6 that provides a mean in-stent diameter stenosis in a human population at 12 months following implantation of less than about 22%, as measured by quantitative coronary angiography.

8. A drug delivery device according to claim 7 that provides a mean in-stent diameter stenosis in a human population at 12 months following implantation of less than about 15%, as measured by quantitative coronary angiography.

9. A method of inhibiting neointimal proliferation in a human coronary artery resulting from percutaneous transluminal coronary angioplasty comprising implanting in the lumen of said coronary artery a drug delivery device comprising: an intraluminal stent; a biocompatible, nonerodible polymeric coating affixed to the intraluminal stent; and from about 64 μg to about 197 μg of rapamycin or a macrocyclic triene analog thereof that binds FKBP12 incorporated into the polymeric coating, wherein said method provides an in-stent late loss in diameter at 12 months following implantation of less than about 0.5 mm, as measured by quantitative coronary angiography.

10. A method according to claim 9 that provides an in-stent late loss in diameter at 12 months following implantation of less than about 0.3 mm, as measured by quantitative coronary angiography.

11. A method according to claim 9 or 10 that provides an in-stent diameter stenosis at 12 months following implantation of less than about 22%, as measured by quantitative coronary angiography.

12. A method according to claim 11 that provides an in-stent diameter stenosis at 12 months following implantation of less than about 15%, as measured by quantitative coronary angiography.

13. A method of inhibiting neointimal proliferation in a coronary artery resulting from percutaneous transluminal coronary angioplasty comprising implanting in the lumen of said coronary artery a drug delivery device comprising: an intraluminal stent; a biocompatible, nonerodible polymeric coating affixed to the intraluminal stent; and from about 64 μg to about 197 μg of rapamycin or a macrocyclic triene analog thereof that binds FKBP12 incorporated into the polymeric coating, wherein said method provides a mean in-stent late loss in diameter in a human population at 12 months following implantation of less than about 0.5 mm, as measured by quantitative coronary angiography.

14. A method according to claim 13 that provides a mean in-stent late loss in diameter in a human population at 12 months following implantation of less than about 0.3 mm, as measured by quantitative coronary angiography.

15. A method according to claim 13 or 14 that provides a mean in-stent diameter stenosis in a human population at 12 months following implantation of less than about 22%, as measured by quantitative coronary angiography.

16. A method according to claim 15 that provides a mean in-stent diameter stenosis in a human population at 12 months following implantation of less than about 15%, as measured by quantitative coronary angiography.

17. The drug delivery device according to any one of claims 1, 2, 4 or 5 wherein said rapamycin or macrocyclic triene analog thereof is incorporated into the polymeric coating at a dose of from about 64 μg to about 125 μg.

18. The drug delivery device according to to any one of claims 1, 2, 4 or 5 that releases a portion of said dose of rapamycin or a macrocyclic triene analog thereof at about six weeks following intraluminal implantation.

19. The drug delivery device according to any one of claims 1, 2, 4 or 5 wherein said rapamycin or macrocyclic triene analog thereof is incorporated into the polymeric coating at a dose of from about 2 μg to about 30 μg per millimeter of stent length.

20. The drug delivery device according to claim 19 wherein said rapamycin or macrocyclic triene analog thereof is incorporated into the polymeric coating at a dose of from about 3 μg to about 13 μg per millimeter of stent length.

21. The drug delivery device according to claim 19 that releases a portion of said dose of rapamycin or a macrocyclic triene analog thereof at about six weeks following intraluminal implantation.

22. The method according to any one of claims 9, 10, 13 or 14, wherein said rapamycin or macrocyclic triene analog thereof is incorporated into the polymeric coating at a dose of from about 64 μg to about 125 μg.

23. The method according to any one of claims 9, 10, 13 or 14, wherein said rapamycin or macrocyclic triene analog thereof is incorporated into the polymeric coating at a dose of from about 2 μg to about 30 μg per millimeter of stent length.

24. The method according to any one of claims 9, 10, 13 or 14, wherein said rapamycin or macrocyclic triene analog thereof is incorporated into the polymeric coating at a dose of from about 3 μg to about 13 μg per millimeter of stent length.

25. The method according to any one of claims 9, 10, 13 or 14, wherein said drug delivery device releases a portion of said dose of rapamycin or a macrocyclic triene analog thereof at about six weeks following intraluminal implantation.

* * * * *